US011826443B2

(12) United States Patent
Manet et al.

(10) Patent No.: US 11,826,443 B2
(45) Date of Patent: Nov. 28, 2023

(54) SOLID COSMETIC COMPOSITION COMPRISING A SILICONE POLYAMIDE, A SILICONE RESIN AND A DISPERSED AQUEOUS PHASE

(71) Applicant: L'OREAL, Paris (FR)

(72) Inventors: Sylvie Manet, Chevilly Larue (FR); Roshanak Debeaud, Chevilly Larue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/471,793

(22) PCT Filed: Dec. 21, 2017

(86) PCT No.: PCT/EP2017/084173
§ 371 (c)(1),
(2) Date: Jun. 20, 2019

(87) PCT Pub. No.: WO2018/115328
PCT Pub. Date: Jun. 28, 2018

(65) Prior Publication Data
US 2020/0113791 A1 Apr. 16, 2020

(30) Foreign Application Priority Data

Dec. 22, 2016 (FR) ..................... 16 63135

(51) Int. Cl.
| | |
|---|---|
| *A61K 8/06* | (2006.01) |
| *A61K 8/02* | (2006.01) |
| *A61K 8/34* | (2006.01) |
| *A61K 8/92* | (2006.01) |
| *A61K 8/36* | (2006.01) |
| *A61K 8/37* | (2006.01) |
| *A61K 8/891* | (2006.01) |
| *A61K 8/898* | (2006.01) |
| *A61Q 1/06* | (2006.01) |
| *A61Q 1/12* | (2006.01) |

(52) U.S. Cl.
CPC ............ *A61K 8/064* (2013.01); *A61K 8/0229* (2013.01); *A61K 8/342* (2013.01); *A61K 8/36* (2013.01); *A61K 8/37* (2013.01); *A61K 8/891* (2013.01); *A61K 8/898* (2013.01); *A61K 8/922* (2013.01); *A61K 8/925* (2013.01); *A61Q 1/06* (2013.01); *A61Q 1/12* (2013.01); *A61K 2800/594* (2013.01)

(58) Field of Classification Search
CPC ....... A61K 8/064; A61K 8/0229; A61K 8/342
See application file for complete search history.

(56) References Cited

U.S. PATENT DOCUMENTS

| | | | |
|---|---|---|---|
| 5,932,197 A * | 8/1999 | Arnaud ................ | A61K 8/8111 424/70.7 |
| 5,981,680 A | 11/1999 | Petroff et al. | |
| 2004/0120912 A1* | 6/2004 | Yu ........................... | A61Q 1/06 424/70.12 |
| 2006/0134028 A1* | 6/2006 | Yu ........................... | A61Q 1/06 424/59 |
| 2012/0321578 A1* | 12/2012 | Leuridan .................. | A61K 8/06 424/63 |
| 2014/0154196 A1* | 6/2014 | Cavazzuti ................ | A61Q 1/02 424/64 |

FOREIGN PATENT DOCUMENTS

| | | |
|---|---|---|
| CN | 1726005 A | 1/2006 |
| FR | 2 918 272 A1 | 1/2009 |
| FR | 2 926 022 A1 | 7/2009 |
| JP | 2013-537214 A | 9/2013 |
| WO | WO2004/060271 A2 | 7/2004 |

OTHER PUBLICATIONS

FR 2 926 022 (machine translation), Jul. 10, 2009, pp. 1-9 (Year: 2009).*
Emalex, Nihon-Emulsion Co, (accessed Jul. 22, 2020) pp. 1-2 (Year: 2020).*
Lochhead, Robert, et al., Cosmetics and Toiletries, (Jan. 29, 2015), pp. 1-18 (Year: 2015).*
Humblebee & me, A Quick Guide to Candelilla Wax and Liquid oil ratios (Apr. 26, 2014) pp. 1-43 (Year: 2014).*

* cited by examiner

*Primary Examiner* — Andrew S Rosenthal
*Assistant Examiner* — Lyndsey M Beckhardt
(74) *Attorney, Agent, or Firm* — POLSINELLI PC

(57) ABSTRACT

This invention relates according to a solid cosmetic composition for makeup or treatment comprising: —a continuous fatty phase comprising at least one silicone polyamide, at least one non-volatile polar hydrocarbon-based oil and at least one polar wax of which the melting point is less than or equal to 90° C.; and—an aqueous phase dispersed in the continuous fatty phase, said silicone polyamide representing at most 9% by weight with respect to the total weight of said composition, and said wax representing at least 7% by weight with respect to the total weight of said composition.

18 Claims, No Drawings

SOLID COSMETIC COMPOSITION COMPRISING A SILICONE POLYAMIDE, A SILICONE RESIN AND A DISPERSED AQUEOUS PHASE

CROSS REFERENCE TO RELATED APPLICATIONS

This application is a National Phase filing under 35 U.S.C. § 371 of PCT/EP2017/084173 filed on 21 Dec. 2017; which application in turn claims priority to Application No. 16 63135 filed in France on 22 Dec. 2016. The entire contents of each application are hereby incorporated by reference.

This invention relates to a solid cosmetic composition, in particular makeup and/or treatment intended to be applied on the skin, lips and skin appendages of humans such as hair, eyelashes, eyebrows or nails, comprising a continuous fatty phase that comprises at least one silicone polyamide, at least one silicone resin, at least one non-volatile polar hydrocarbon-based oil and at least one polar wax with a melting point less than or equal to 90° C.; and an aqueous phase dispersed in the continuous fatty phase, said silicone polyamide representing at most 9% of the total weight of said composition, and said wax representing at least 7% of the total weight of said composition.

In makeup or care cosmetic products, it is common to find a structured liquid phase, namely gelled and/or stiffened. This is in particular the case with solid compositions, in particular solid cast composition, balms and lipsticks, eye shadows, anti-wrinkle products and cast foundations. This structuring is in particular obtained using specific gelling agents, such as for example silicone polymers of the polysiloxane/polyamide type.

The use of this type of silicone polymer makes it possible to access an original solid texture of cosmetic composition: indeed, this texture does not correspond to that of a conventional stick provided with a relatively high stiffness, or to that of a conventional gel of which the consistency is liquid or pasty.

In document EP2044976, solid cosmetic compositions are proposed that have a structured liquid phase. Indeed, these compositions comprise an oily phase gelled by a silicone polymer of the polysiloxane/polyamide type and a tackifying resin in particular of the colophony type, in order to increase the hardness of the composition. However, these compositions can be tacky when applied.

It is also known to associate silicone polymers of the polysiloxane/polyamide type with silicon resins in order to increase the stability of these compositions. However, they tend to be more difficult to apply, to be tacky when applied, and cause feelings of dryness, which is not comfortable for the users.

Furthermore, most of the solid compositions of lip makeup, such as lipsticks, are anhydrous. However, for various reasons linked in particular to a better comfort of use (in particular an effect of freshness, and a feeling of hydration and others), it is interesting to incorporate an aqueous phase. However, no additional benefit linked to this addition is generally obtained.

As such, there is a need for a solid cosmetic formulation, in particular for lip makeup, which is provided with good stretchability qualities for an easy and pleasant application, while still being non-tacky, and conferring freshness and hydration to the application. Furthermore, there is a need for such a composition that furthermore has good stability over time, and which does migrate or migrates very little.

Unexpectedly, the inventors have succeeded in accessing such a formulation, which makes it possible to resolve the aforementioned problems.

Consequently, this invention relates according to a first aspect to a solid cosmetic composition for makeup or treatment comprising:

a continuous fatty phase comprising at least one silicone polyamide, at least one silicone resin, at least one non-volatile polar hydrocarbon-based oil and at least one polar wax of which the melting point is less than or equal to 90° C.; and an aqueous phase dispersed in the continuous fatty phase, said silicone polyamide representing at most 9% by weight with respect to the total weight of said composition, and said wax representing at least 7% by weight with respect to the total weight of said composition.

The term "solid" characterizes the state of the composition at ambient temperature (25° C.) and at atmospheric pressure (760 mm of Hg).

More preferably, the silicone polyamide is between 2 and 20% by weight, preferably between 3 and 7%, by weight in relation to the total weight of the composition.

This invention only has for object a method for makeup or treatment of keratin materials and in particular lips wherein on the keratin materials, and in particular the lips, a composition such as defined herein above is applied.

The invention makes it possible to obtain solid compositions that have a good slip and the application thereof is pleasant.

In addition, when the composition is applied, there is no feeling of a substantial sliding effect without feeling a deposit of the composition (it is said that the application does not "chase" when it is applied).

The compositions according to the invention provide a hydration and freshness to the application.

Moreover, no feeling of dryness of the deposit is felt or any tautness once the composition is applied.

The deposit obtained is fresh, fine, homogeneous, not tacky. It makes it possible to obtain a deposit with homogeneous coloration, that does not migrate and with good stability, and which also has good covering power.

The solid compositions in accordance with the invention furthermore have a hardness that is weaker than that of conventional sticks. Advantageously, the compositions according to the invention have a hardness varying from 10 to 100 g, preferably varying from 30 to 70 g, contrary to conventional sticks that have a hardness greater than 100 g, in particular more than 150 g. This hardness confers on the solid composition according to the invention sufficiently low stiffness in order to obtain a deposit that has the qualities mentioned in the preceding paragraph, which still being high enough to not break.

Characterization of the Hardness

Advantageously, the compositions according to the invention have a hardness varying from 20 to 90 $Nm^{-1}$, more particularly 30 to 80 $Nm^{-1}$, preferably from 40 to 60 $Nm^{-1}$, and more advantageously from 45 to 55 $Nm^{-1}$.

The hardness of the composition according to the invention is such that the composition is self-supporting and can be broken down easily in order to form a satisfactory deposit on the skin and the lips. Furthermore, with this hardness, the composition of the invention resists impacts well.

The hardness is measured according to the following protocol:

The lipstick is stored at 20° C. for 24 hours before the hardness measurement is taken.

The hardness can be measured at 20° C. using the so-called "wire to cut the butter" method, which consists in transversally cutting a stick of the product, preferably cylindrical revolution, using a rigid tungsten wire with a diameter of 250 μm by displacing the wire relatively to the stick at a speed of 100 mm/min.

The hardness of the samples of the compositions of the invention, expressed in $Nm^{-1}$, is measured by means of a DFGS2 dynamometer sold by INDELCO-CHATILLON.

The measurement is reproduced three times and then averaged. The average of the three values read using the dynamometer mentioned hereinabove, noted as Y, is given in grams. This average is converted into Newtons then divided by L which represents the highest dimension passed through by the wire. In the case of a cylindrical stick, L is equal to the diameter (in meters).

The hardness is converted into $Nm^{-1}$ by the equation hereinbelow:

$$(Y \times 10^{-3} \times 9.8)/L$$

For a measurement at a different temperature, the stock is stored 24 hours at this new temperature before the measurement.

Silicone Polyamide

As indicated hereinabove, the compositions according to the invention comprise at least one silicone polyamide.

The silicone polyamides of the composition are preferably solid at ambient temperature (25° C.) and atmospheric pressure (760 mm of Hg).

The term "polymer" in terms of the invention means a compound that has at least 2 repeat units, preferably at least 3 repeat units and more preferably 10 repeat units.

The silicone polyamides of the composition of the invention can be polymers of the polyorganosiloxane type such as for example those described in documents U.S. Pat. Nos. 5,874,069, 5,919,441, 6,051,216 and 5,981,680. According to the invention, the silicone polymers can belong to the following two families:

(1) polyorganosiloxanes comprising at least two amide groups, with these two groups being located in the chain of the polymer, and/or
(2) polyorganosiloxanes comprising at least two amide groups, with these two groups being located on grafts or branches.

A) According to a first alternative, the silicone polyamides are polyorganosiloxanes such as defined hereinabove and of which the amide units are arranged in the chain of the polymer.

The silicon polyamides can more particularly be polymers comprising at least one pattern that satisfies the general formula I:

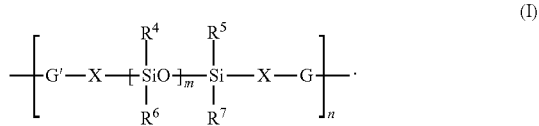

(I)

1) in which: G' is C(O) when G is —C(O)—NH—Y—NH— and G' is —NH— when G is —NH—C(O)—Y—C(O)—
2) $R^4$, $R^5$, $R^6$ and $R^7$, identical or different, are a group chosen from:
   the $C_1$ to $C_{40}$, linear, branched or cyclic, saturated or unsaturated hydrocarbon groups, that can contain in their chain one or several atoms of oxygen, sulfur and/or nitrogen, and which can be partially or entirely substituted with fluorine atoms,
   the $C_6$ to $C_{10}$ aryl groups, possibly substituted with one or several $C_1$ to $C_4$ alkyl groups,
   the polyorganosiloxane chains containing or not one or several atoms of oxygen, sulfur and/or nitrogen,
3) the X, identical or different, are a $C_1$ to $C_{30}$, linear or branched alkylene di-yl group that can contain in its chain one or several atoms of oxygen and/or nitrogen,
4) Y is a $C_1$ to $C_{50}$ linear or branched, arylene, cycloalkylene, alkylarylene or arylalkylene, saturated or unsaturated, alkylene divalent group, that can contain one or several atoms of oxygen, sulfur and/or nitrogen, and/or carry as a substitute one of the following atoms or groups of atoms: fluorine, hydroxy, $C_3$ to $C_8$ cycloalkyl, $C_1$ to $C_{40}$ alkyl, $C_5$ to $C_{10}$ aryl, phenyl possibly substituted with 1 to 3 $C_1$ to $C_3$ alkyl groups, $C_1$ to $C_3$ hydroxyalkyl and $C_1$ to $C_6$ amino alkyl, or
5) Y is a group having the formula:

wherein
T is a $C_3$ to $C_{24}$ linear or branched, saturated or unsaturated, trivalent or tetravalent hydrocarbon group, possibly substituted with a polyorganosiloxane chain, and that can contain one or several atoms chosen from O, N and S, where T is a trivalent atom chosen from N, P and Al, and
$R^8$ is a $C_1$ to $C_{50}$, linear or branched, alkyl group or a polyorganosiloxane chain, that can contain one or several ester, amide, urethane, thiocarbamate, urea, thiourea and/or sulfonamide groups that be bound or not to another polymer chain,
6) n is an integer ranging from 2 to 500, preferably from 2 to 200, and m is an integer ranging from 50 to 1000, preferably from 50 to 700 and even better from 50 to 200.

Note that "m" corresponds to the average degree of polymerization of the silicone portion of the silicone polyamide.

According to an embodiment of the invention, 80% of the $R^4$, $R^5$, $R^6$ and $R^7$, of the polymer are chosen preferably from the methyl, ethyl, phenyl and 3,3,3-trifluoropropyl groups. According to another embodiment, 80% of the $R^4$, $R^5$, $R^6$ and $R^7$, of the polymer are methyl groups.

According to the invention, Y can be various divalent groups, possibly comprising in addition one or two free valencies in order to establish bonds with other patterns of the polymer or copolymer. Preferably, Y is a group chosen from:

a) $C_1$ to $C_{20}$, preferably $C_1$ to $C_{10}$, linear alkylene groups,
b) branched alkylene groups that can contain $C_{30}$ to $C_{56}$ non-conjugated cycles and unsaturations,
c) $C_5C_6$ cycloalkylene groups,
d) phenylene groups possibly substituted with one or several $C_1$ to $C_{40}$ alkyl groups,
e) $C_1$ to $C_{20}$ alkylene groups, comprising from 1 to 5 amide groups,
f) $C_1$ to $C_{20}$ alkylene groups, comprising one or several substituents, chosen from the $C_3$ to $C_8$ hydroxyl, cycloalkan, $C_1$ to $C_3$ hydroxyalkyl and $C_1$ to $C_6$ alkylamine groups, g) polyorganosiloxane chains having the formula:

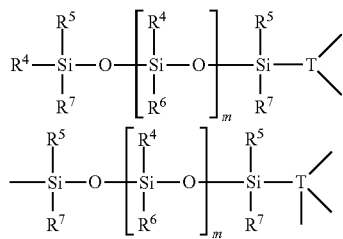

in which $R^4$, $R^5$, $R^6$, $R^7$, T and m are such as defined hereinabove.

B) According to the second alternative, the silicone polyamides can be polymers comprising at least one pattern that satisfies the formula (II):

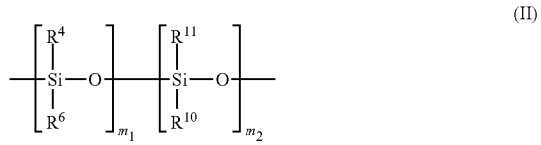

(II)

wherein
- $R^4$ and $R^6$, identical or different, are such as defined hereinabove for the formula (I),
- $R^{10}$ is a group such as defined hereinabove for $R^4$ and $R^6$, or is the group having formula $XG''R^{12}$ wherein X are such as defined hereinabove for the formula (I) and $R^{12}$ is a hydrogen atom or a $C_1$ to $C_{50}$ linear, branched or cyclic, saturated or unsaturated hydrocarbon group, possibly comprising in its chain one or several atoms chosen from O, S and N, possibly substituted with one or several fluorine atoms and/or one or several hydroxyl groups, or a phenyl group possibly substituted with one or several $C_1$ to $C_4$ alkyl groups, and G'' is —C(O)NH and —HNC(O).
- $R^{11}$ is the group having formula $XG''R^{12}$ wherein X, G'' and $R^{12}$ are such as defined hereinabove,
- $m_1$ is an integer varying from 50 to 998, and
- $m_2$ is an integer varying from 2 to 500.

Note that "$m_1$" corresponds to the average degree of polymerization of the silicone portion of the silicone polyamide.

According to the invention, the silicone polymer can be a homopolymer, i.e. a polymer that comprises several identical patterns, in particular patterns having formula (I) or formula (II).

According to the invention, it is also possible to use a polymer constituted by a copolymer that comprises several different patterns having formula (I), i.e. a polymer wherein at least one of the $R^4$, $R^5$, $R^6$, $R^7$, X, G, Y, m and n is different in one of the patterns. The copolymer can also be formed of several patterns having formula (II), wherein at least one of $R^4$, $R^6$, $R^{10}$, $R^{11}$, $m_1$ and $m_2$ is different in at least one of the patterns.

A polymer comprising at least one pattern having formula (I) and at least one pattern having formula (II) can also be used, with the patterns having formula (I) and the patterns having formula (II) able to be identical or different from one another.

According to an alternative of the invention, a silicone polyamide can also be used comprising more or less one hydrocarbon pattern comprising two groups able to establish hydrogen interactions chosen from the ester, amide, sulfonamide, carbamate, thiocarbamate, urea, urethane, thiourea, oxamido, guanidino, biguanidino groups and combinations thereof.

These copolymers can be block polymers, sequenced polymers or grafted polymers.

In the formulas (I) and (II), the alkylene group representing X or Y can possibly contain in its alkylene portion at least one of the following elements:
1) 1 to 5 amide, urea, urethane, or carbamate groups,
2) a $C_5$ or $C_6$ cycloalkyl group, and
3) a phenylene group possibly substituted with 1 to 3 identical or different $C_1$ to $C_3$ alkyl groups.

In formulas (I) and (II), the alkylene groups can also be substituted with at least one element chosen from the group comprising:
- a hydroxy group,
- a $C_3$ to $C_8$ cycloalkyl group,
- one to three $C_1$ to $C_{40}$ alkyl groups,
- a phenyl group possibly substituted with one to three $C_1$ to $C_3$ alkyl groups,
- a $C_1$ to $C_3$ hydroxyalkyl group, and
- a $C_1$ to $C_6$ aminoalkyl group.

In these formulas (I) and (II), Y can also be:

where $R^8$ is a polyorganosiloxane chain, and T is a group having formula:

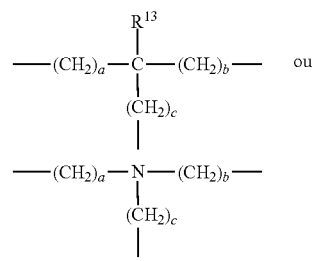

ou wherein a, b and c are independently integers ranging from 1 to 10, and $R^{13}$ is a hydrogen atom or a group such as those defined for $R^4$, $R^5$, $R^6$ and $R^7$.

In formulas (I) and (II), $R^4$, $R^5$, $R^6$ and $R^7$ are preferably, independently, a $C_1$ to $C_{40}$ linear or branched alkyl group, preferably a $CH_3$, $C_2H_5$, $nC_3H_7$ or isopropyl group, a polyorganosiloxane chain or a phenyl group possibly substituted with one to three methyl or ethyl groups.

As has been seen hereinabove, the polymer can comprise identical or different patterns having formula (I) or (II).

As such, the polymer can be a polyamide containing several patterns having formula (I) or (II) of different lengths, or a polyamide that satisfies the formula (III):

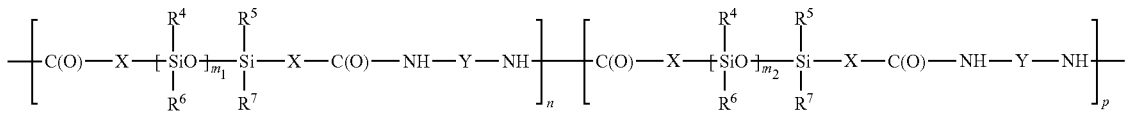

wherein X, Y, n, $R^4$ to $R^7$ have the meanings given hereinabove, $m_1$ and $m_2$ which are different, are chosen from the range from 1 to 1000, and p is an integer ranging from 2 to 300.

In this formula, the patterns can be structured to form either a block copolymer, or a random copolymer or an alternating copolymer. In this copolymer, the patterns can be not only of different lengths but also of different chemical structures, for example having different Ys. In this case, the polymer can satisfy the formula (IV):

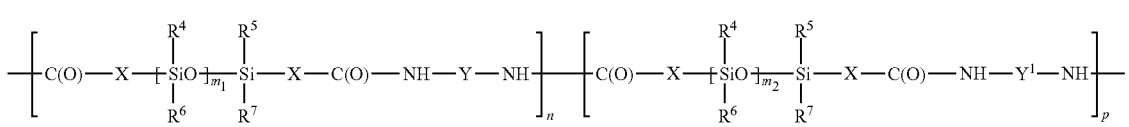

wherein $R^4$ to $R^7$, X, Y, $m_1$, $m_2$, n and p have the meanings given hereinabove and $Y^1$ is different from Y but chosen from the groups defined for Y. As hereinabove, the various patterns can be structured to form either a block copolymer, or a random copolymer or an alternating copolymer.

In this first embodiment of the invention, the silicon polymer can also be constituted by a grafted copolymer. As such, the polyamide with silicone units can be grafted and possibly cross-linked by silicone chains to amide groups. Such polymers can be synthesized with trifunctional amines.

According to the invention, as has been seen hereinabove, the silicone units can be in the main or backbone chain of the polymer, but they can also be present in grafted or pendant chains. In the main chain, the siloxane units can be in the form of segments as described hereinabove. In pendant or grafted chains, the siloxane units can appear individually or in segments According to an alternative embodiment of the invention, a silicone polyamide and hydrocarbon polyamide copolymer can be used, or a copolymer comprising patterns having formula (I) or (II) and hydrocarbon polyamide patterns. In this case, the silicone polyamide patterns can be arranged at the ends of the hydrocarbon polyamide.

Advantageously, the composition comprises at least one polyamide/polydimethylsiloxane polymer, in particular a polymer having general formula (I) that has an index m with a value greater than 50, in particular greater than 75, in particular greater than about 100.

Advantageously, the silicone polyamide having formula (I) has a mean molar mass ranging from 10,000 to 500,000 g/mol.

More preferably, X and Y independently are a group chosen from the $C_1$ to $C_{20}$, preferably $C_1$ to $C_{10}$ linear alkylene groups.

As examples of silicone polyamide, mention can be made of one of the silicone polyamides obtained in accordance with the examples 1 to 3 of document U.S. Pat. No. 5,981,680, as well as the product sold under the reference DC 2-8179 by Dow Corning (INCI name: NYLON-611/DIMETHICONE COPOLYMER).

According to an alternative embodiment of the invention, the polymer consists of a homopolymer or copolymer comprising urethane or urea groups. These polymers are described in detail in application WO 2003/106614.

The composition can contain in place of the silicone polyamide a polyorganosiloxane polymer that contains two or several urethane and/or urea groups, either in the backbone of the polymer, or on the side chains or as pendant groups.

Polymers that contain at least two urethane and/or urea groups in the backbone can be polymers comprising at least one pattern that satisfies the following formula:

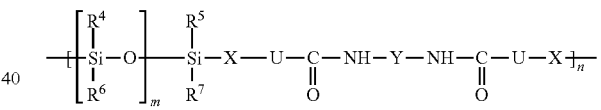

wherein $R^4$, $R^5$, $R^6$, $R^7$, X, Y, m and n have the meanings given hereinabove for the formula (I), and U is O or —NH, so that:

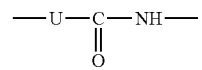

corresponds to a urethane or urea group.

In this formula, Y can be a $C_1$ to $C_{40}$ linear or branched alkylene group, possibly substituted by a $C_1$ to $C_{15}$ alkyl group or a $C_5$ to $C_{10}$ aryl group. Preferably, a $(CH_2)_6$ group is used.

The polymer constituting the silicone polymer can be formed from silicone urethane and/or silicone urea patterns of a different length and/or constitution, and have the form of block, sequenced or statistic (random) copolymers. As in the case of silicone polyamides having formula (I), (II) or (Ill), polyurethanes or silicone polyurea can be used in the invention that have patterns of a different length and structure, in particular patterns of different lengths by the number of silicone units.

The polymers and copolymers used in the composition of the invention advantageously have a transition temperature from the solid state to the liquid state ranging from 45° C. to 190° C. Preferably, they have a transition temperature from the solid state to the liquid state ranging from 70 to 130° C. and better from 80° C. to 105° C.

Silicone polyamide is present in the composition in a content of at most 9% by weight in relation to the total weight of the composition.

The silicone polyamide can be present in the composition in a total content ranging from 2% to 9% by weight, advantageously from 2% to 7% by weight, and preferably from 3% to 6% by weight in relation to the total weight of the composition.

Advantageously, the silicone polyamide has a mean molar mass by weight between 10,000 and 500,000 g/mol.

Silicone Resin

The composition according to the invention comprises at least one silicone resin.

More generally, the term "resin", refers to a compound of which the structure is three-dimensional. As such, in terms of this invention, a polydimethylsiloxane is not a silicone resin.

The classification of silicone resins (also called siloxane resins or silicone resins) is known under the name "MDTQ", the resin being described according to the various siloxane monomeric units comprised therein, each of the letters "MDTQ" characterizing a type of unit.

The "letter M" represents the Monofunctional unit having the formula $R1R2R3SiO_{1/2}$, the silicon atom being bound to a single oxygen atom in the polymer comprising this unit.

The letter "D" denotes a Difunctional unit $R1R2SiO_{2/2}$ wherein the silicon atom is bound to two oxygen atoms.

The letter "T" represents a Trifunctional unit having the formula $R1SiO_{3/2}$.

Such resins are described for example in "Encyclopedia of Polymer Science and Engineering, vol. 15, John and Wiley and Sons, New York, (1989), p. 265-270, and U.S. Pat. Nos. 2,676,182, 3,627,851, 3,772,247, 5,248,739 or U.S. Pat. Nos. 5,082,706, 5,319,040, 5,302,685 and 4,935,484.

In the M, D, T patterns defined previously, Ri, namely R1, R2 and R3, identical or different, represent a hydrocarbon radical (in particular alkyl) having from 1 to 10 carbon atoms, a phenyl group, a phenylalkyl group or a hydroxyl group.

Finally, the letter "Q" denotes a Tetrafunctional unit $SiO_{4/2}$ wherein the silicon atom is bound to four oxygen atoms in turn bound to the remainder of the polymer.

Various silicone resins having different properties may be obtained from these various units, the properties of these polymers varying according to the type of monomers (or units), the type and number of the Ri radical or radicals, the polymer chain length, the degree of branching and the pendant chain size.

In terms of the silicon resins that can be used in the compositions according to the invention use can be made for example of silicone resins of the MQ type, of the T type or of the MQT type.

MQ Resins:

In terms of silicone resins of the MQ type, mention can be made of alkylsiloxysilicates having formula $[(R1)_3SiO_{1/2}]_x$ $(SiO_{4/2})_y$ (MQ units) wherein x and y are integers ranging from 50 to 80, and such that the R1 group is a radical such as defined hereinabove, and preferably is an alkyl group that has from 1 to 8 carbon atoms, or a hydroxyl group, preferably, a methyl group, As examples of solid silicone resins of the MQ type of the trimethylsiloxysilicate type, mention can be made of those sold under the reference SR1000 by General Electric, under the reference TMS 803 by Wacker, under the name "KF-7312J" by Shin-Etsu, "DC 749", "DC 593" by Dow Corning.

Like the silicone resins comprising MQ siloxysilicate patterns, mention can also be made of phenylalkylesiloxysilicate resins, such as phenylpropyldimethylsiloxysilicate (Silshine 151 sold by General Electric). The preparation of such resins is described in particular in U.S. Pat. No. 5,817,302.

T Resins:

As examples of silicone resins of the T type, mention can be made of polysilsesquioxanes having formula $(RSiO_{3/2})_x$ (T units) wherein x is greater than 100 and such that the R group is an alkyl group having from 1 to 10 carbon atoms, said polysilsesquioxanes can furthermore include Si—OH terminal groups.

Mention can also be made of polymethylsilsesquioxanes which are polysilsesquioxanes wherein none of the methyl radicals is substituted by another group. Such polymethylsilsesquioxanes are described for example in the document U.S. Pat. No. 5,246,694.

Preferably, polymethylsilsesquioxane resins can be used wherein R is a methyl group, such as for example those sold:
— by Wacker under the reference Resin MK such as Belsil PMS MK: polymer comprising $CH_3SiO_{3/2}$ repetitive units (T units), that may also comprise up to 1% by weight of $(CH_3)_2SiO_{2/2}$ units (D units) and having a mean molecular weight of approximately 10,000 g/mol, or
— by SHIN-ETSU under the references KR-220L consisting of T units having the formula $CH_3SiO_{3/2}$ and having Si—OH (silanol) terminal groups, under the reference KR-242A comprising 98% T units and 2% D dimethyl units and having Si—OH terminal units or under the reference KR-251 comprising 88% T units and 12% D dimethyl units and having Si—OH terminal groups.

MQT Resins:

As a resin comprising MQT patterns, those mentioned in document U.S. Pat. No. 5,110,890 are known.

A preferred form of resins of the MQT type are the MQT-propyl resins (also called MQTPr). Such resins that can be used in the compositions according to the invention are in particular those described and prepared in application WO 2005/075542, of which the content is incorporated here by reference.

The MQ-T-propyl resin preferably comprises the units:
(i) $(R1_3SiO_{1/2})_a$
(ii) $(R2_2SiO_{2/2})_b$
(iii) $(R3SiO_{3/2})_c$ and
(iv) $(SiO_{4/2})_d$
with
R1, R2 and R3 independently are a hydrocarbon radical (in particular alkyl) having from 1 to 10 carbon atoms, a phenyl group, a phenylalkyl group or a hydroxyl group and preferably an alkyl radical having from 1 to 8 carbon atoms or a phenyl group,
a, b, c and d being molar fractions,
a is between 0.05 and 0.5,
b is between zero and 0.3,
c is greater than zero,
d is between 0.05 and 0.6,
a+b+c+d=1,
with the condition that more than 40% in moles of the R3 groups of the siloxane resin are propyl groups.

Preferably, the siloxane resin comprises the units:
(i) $(R1_3SiO_{1/2})_a$
(iii) $(R3SiO_{3/2})_c$ and
(iv) $(SiO_{4/2})_d$
with
R1 and R3 independently are an alkyl group having from 1 to 8 carbon atoms, R1 being preferably a methyl group and R3 preferably being a propyl group,
a being between 0.05 and 0.5, preferably between 0.15 and 0.4,
c being greater than zero, preferably between 0.15 and 0.4,
d being between 0.05 and 0.6, preferably between 0.2 and 0.6, or between 0.2 and 0.55,
a+b+c+d=1, and a, b, c and d being molar fractions,
with the condition that more than 40% in moles of the R3 groups of the siloxane resin are propyl groups.

The siloxane resins can be used according to the invention can be obtained by a method comprising the reaction of:
A) an MQ resin comprising at least 80% in moles of units $(R1_3SiO_{1/2})_a$ and $(SiO_{4/2})_d$
R1 being an alkyl group having from 1 to 8 carbon atoms, an aryl group, a
carbinol group or an amino group,
a and d being greater than zero,
with the a/d ration being between 0.5 and 1.5;
and of
B) a propyl T resin comprising at least 80% in moles of units $(R3SiO_{3/2})_c$,
R3 being an alkyl group having from 1 to 8 carbon atoms, an aryl group, a carbinol group or an amino group,
c is greater than zero,
with the condition that at least 40% in moles of the R3 groups are propyl groups,
where the A/B mass ratio is comprised between 95:5 and 15:85, preferably the A/B mass ratio is 30:70.

Advantageously, the A/B mass ration is between 95:5 and 15:85. Preferably, the A/B ratio is less than or equal to 70:30. These preferred ratios have shown to allow for comfortable deposits.

Preferably, the composition according to the invention comprises, as a silicone resin, at least one resin of the MQ type such as described hereinabove.

In particular, the silicone resin is a siloxysilicate resin, preferably a trimethylsiloxysilicate resin.

Advantageously, the silicone resin is present in a content of at least 5% by weight, preferably with a content ranging from 5 to 15% by weight in relation to the total weight of the composition, or better from 6 to 9% by weight.

Preferably the silicone resin, and in particular the trimethylsiloxysilicate resin, is present in a ratio such that the silicon resin/silicone polyamide mass proportion is between 1 and 7/3, and preferably between 1.2 and 2.

Continuous Fatty Phase

The continuous fatty phase of the composition according to the invention comprises the silicone polyamide and the silicone resin indicated hereinabove, as well as at least one wax, and at least one non-volatile polar hydrocarbon-based oil.

Non-Volatile Polar Hydrocarbon-Based Oil

Preferably, the composition comprises 5% to 30%, preferably 5% to 25% by weight of non-volatile polar hydrocarbon-based oil with respect to the total weight of the composition.

"Oil" refers to a non-aqueous compound, liquid at 25° C. at atmospheric pressure ($1.013 \cdot 10^5$ Pa), not water-miscible.

"Not miscible" means that the mixture of the same quantity of water and oil, after agitation, does not lead to a stable solution that comprises only a single phase, in the aforementioned conditions of temperature and pressure. The observation is made with the unaided eye or using a phase contrast microscope if necessary, over 100 g of mixture obtained after Rayneri stirring sufficient to cause a vortex to appear within the mixture (for the purposes of information 200 to 1000 rpm; with the resulting mixture being left to sit, in a closed bottle, for 24 hours at ambient temperature before observation.

"Non-volatile oil" refers to an oil of which the vapor pressure at 25° C. and atmospheric pressure, is not zero and less than $10^{-3}$ mm of Hg (0.13 Pa). By way of example, the vapor pressure may be measured according to the static method or the method of effusion by isothermic thermogravimetry, according to vapor pressure (norm OECD 104).

The term "hydrocarbon-based oil" refers to an oil essentially formed, or consisting, of carbon and hydrogen atoms, and optionally oxygen, nitrogen atoms, and containing no silicon or fluorine. The hydrocarbon-based oil is therefore separate from a silicone oil and from a fluorine oil.

It may contain alcohol, ester, ether, carboxylic acid, amine and/or amide groups.

Preferably, the hydrocarbon-based oil is free of heteroatoms such as nitrogen, sulfur and phosphorus.

In this case, the non-volatile polar hydrocarbon-based oil comprises at least one oxygen atom.

In particular, this hydrocarbon-based non-volatile oil comprises at least one alcohol function (it is then an "alcohol oil") or at least one ester function (it is then an "ester oil").

The ester oils that can be used in the compositions according to the invention can in particular be hydroxylated.

The composition can comprise one or several non-volatile hydrocarbon-based oils, in particular chosen from:

$C_{10}$-$C_{26}$ alcohols, preferably monoalcohols;

More particularly, the $C_{10}$-$C_{26}$ alcohols are saturated or not, branched or not, and comprise from 10 to 26 carbon atoms.

Preferably, the $C_{10}$-$C_{26}$ alcohols are fatty alcohols, preferably branched when they contain at least 16 carbon atoms.

As examples of fatty alcohols that can be used according to the invention, mention can be made of linear or branched fatty alcohols, or natural such as for example alcohols coming from plant substances (coconut, palm, etc.) or animal substances (tallow, etc.).

Of course, other long-chain alcohols can also be used, such as for example ether-alcohols or so-called Guerbet alcohols.

Finally, certain more or less long cuts of alcohols of natural origin, such as for example coco ($C_{12}$ to $C_{16}$) or tallow ($C_{16}$ to $C_{18}$) or compounds of the diol or cholesterol type, can also be used.

Preferably a fatty alcohol comprising from 10 to 24 carbon atoms, and more preferably from 12 to 22 carbon atoms is used.

As particular examples of fatty alcohols that can be used preferably, mention can be made in particular of lauric, isostearyl, oleic alcohol, 2-butyloctanol, 2-undecyl pentadecanol, 2-hexyldecylic alcohol, isocetylic alcohol, octyldodecanol and mixtures thereof.

According to one advantageous embodiment of the invention, the alcohol is chosen from octyldodecanol.

monoesters, diesters, triesters, optionally hydroxylated, of a $C_2$—C mono or polycarboxylic acid and a $C_2$-$C_8$ alcohol.

In particular:

monoesters of a $C_2$-$C_8$ carboxylic and of a $C_2$-$C_8$ alcohol, optionally hydroxylated, the diesters of a $C_2$-$C_8$ carboxylic diacid and of a $C_2$-$C_8$ alcohol, optionally hydroxylated; such as diisopropyl adipate, diethyl-2 hexyl adipate, dibutyl adipate, or diisostearyl adipate, 2-diethyl-hexyl succinate, the triesters of a $C_2$-$C_8$ carboxylic triacide and of a $C_2$-$C_8$ alcohol, optionally hydroxylated, such as the esters of citric acid, such as trioctyl citrate, triethylcitrate, acetyltributyl citrate, tributyl citrate, acetyltributyl citrate.

The esters of a $C_2$-$C_8$ polyol and of one or several $C_2$-$C_8$ carboxylic acids, such as the diesters of glycol and of monoacids, such as neopentylglycol diheptanoate, or the triesters of glycol and of monoacids such as triacetine.

the ester oils, in particular having between 17 and 70 carbon atoms.

As examples, mention can be made of mono-, di- or tri-esters.

Ester oils can be hydroxylated or not.

The non-volatile ester oil can be chosen for example from:

monoesters comprising between 17 and 40 carbon atoms in total, in particular monoesters, having formula $R_1COOR_2$ wherein $R_1$ is the remainder of a linear or branched or aromatic fatty acid comprising from 4 to 40 carbon atoms, saturated or not, and $R_2$ is a hydrocarbon chain in particular branched containing from 3 to 40 carbon atoms with the condition that $R_1+R_2$ is 17, as for example Purcellin oil (cetostearyl octanoate), isononyl isononanoate, $C_{12}$ to $C_{15}$ alcohol benzoate, 2-ethyl hexyl palmitate, octyldodecyl neopentanoate, octyl-2-dodecyl stearate, octyl-2-dodecyl erucate, isostearyl isostearate, octyl-2 dodecyl benzoate, octanoates, decanoates or ricinoleates of alcohols or of polyalcohols, isopropyl myristate, isopropyl palmitate, butyl stearate, hexyl laurate, 2-ethylhexyl palmitate, 2-hexyl decyl laurate, 2-octyldodecyl palmitate, 2-octyldodecyl myristate.

Preferably, these are esters having formula $R_1COOR_2$ wherein $R_1$ is the remainder of a linear or branched fatty acid comprising from 4 to 40 carbon atoms and $R_2$ is a hydrocarbon chain in particular branched containing from 3 to 40 carbon atoms, with $R_1$ and $R_2$ being such that $R_1+R_2$ is 17.

More particularly, the ester comprises between 17 and 40 carbon atoms in total.

As preferred monoesters, mention can be made of isononyl isononanoate, oleyl erucate and/or octyl-2-docecyl neopentanoate;

fatty acid monoesters, in particular from 18 to 22 carbon atoms, and in particular lanolic acid, oleic acid, lauric acid, stearic acid, and diols, such as propylene glycol monoisostearate.

diesters, in particular comprising between 18 and 60 carbon atoms in total, in particular between 18 and 50 carbon atoms in total. In particular diesters of carboxylic diacid and of monoalcohols can be used, such as preferably diisostearyl malate, or the diesters of glycol and of monocarboxylic acids, such as neopentylglycol diheptanoate, propylene glycol dioctanoate, diethylene glycol diisononanoate, or polyglyceryl-2 diisostearate (in particular such as the compound sold under the commercial reference DERMOL DGDIS by Alzo);

hydroxylated monoesters and diesters, preferably having a total number of carbon ranging from 18 to 70, such as polyglyceryl-3 diisostearate, isostearyl lactate, octylhydroxystearate, octyldodecyl hydroxystearate, diisostearyl malate, glyceryl stearate;

triesters, in particular comprising between 35 and 70 carbon atoms in total, in particular such as triesters of carboxylic triacide, such as triisostearyl citrate, or tridecyl trimellitate, or triesters of glycol and of monocarboxylic acids such as polyglyceryl-2 triisostearate;

tetraesters, in particular having a total number of carbon ranging from 35 to 70, such as tetraesters of pentaerythritol or of polyglycerol and of a monocarboxylic acid, for example such as pentaerythrityl tetrapelargonate, pentaerythrityl tetraisostearate, pentaerythrityl tetraisononanoate, glyceryl tri decyl-2 tetradecanoate, polyglyceryl-2 tetraisostearate or pentaerythrityl tetra decyl-2 tetradecanoate;

polyesters obtained by condensing unsaturated fatty acid dimers and/or trimers and diol such as those described in the patent application FR 0 853 634, such as in particular dilinoleic acid and 1,4-butanediol. Mention may particularly be made in this respect of the polymer sold by Biosynthesis under the name Viscoplast 14436H (INCI name: dilinoleic acid/butanediol copolymer), or polyol and diacid dimer copolymers, and esters thereof, such as Hailuscent ISDA;

dimer diol and mono- and dicarboxylic esters and polyesters, such as dimer diol and fatty acid esters and dimer diol esters carboxylic diacid dimers, in particular that can be obtained from a carboxylic diacid dimer particularly derived from the dimerization of an unsaturated fatty acid, particularly $C_8$ to $C_{34}$, particularly $C_{12}$ to $C_{22}$, in particular $C_{16}$ to $C_{20}$, and more particularly $C_{18}$, such as dilinoleic diacid esters and dilinoleic diol dimers, for example such as those sold by NIPPON FINE CHEMICAL under the trade name LUSPLAN DD-DA5® and DD-DA7®;

polyesters resulting from the esterification of at least one triglyceride of carboxylic acid(s) hydroxylated by an aliphatic monocarboxylic acid and by an aliphatic dicarboxylic acid, possibly unsaturated such as castor oil of succinic acid and of isostearic acid sold under the reference Zenigloss by Zenitech;

plant-based hydrocarbon-based oils such as fatty acid liquid triglycerides (liquid at ambient temperature), in particular fatty acids having from 7 to 40 carbon atoms, such as heptanoic or octanoic acid triglycerides or jojoba oil, in particular, mention can be made of saturated triglycerides such as caprylic/capric triglyceride and mixtures thereof, for example such as the one sold under the reference Myritol 318 from Cognis, glycerol triheptanoate, glycerin trioctanoate, triglycerides of acid in $C_{18-36}$ such as those sold under the reference DUB TGI 24 sold by Stearineries Dubois), and unsaturated triglycerides such as castor oil, olive oil, ximenia oil, pracaxi oil.

vinylpyrrolidone/1-hexadecene copolymers, such as for example the one sold under the name ANTARON V-216 (also called Ganex V216) by ISP (MW=7,300 g/mol).

dialkyl carbonates, the 2 alkyl chains possibly being identical or different, such as the dicaprylyl carbonate sold under the name Cetiol CC®, by Cognis.

and mixtures thereof.

Preferably, the non-volatile polar hydrocarbon-based oil or oils, are chosen from $C_{10}$-$C_{26}$ monoalcohols, ester oils, and in particular monoesters comprising at least 17 carbon atoms in total, diesters, hydroxylated or not, comprising at least 18 carbon atoms in total, triesters, in particular having at least 35 carbon atoms, tetraesters, in particular having at least 35 carbon atoms, as well as mixtures thereof.

According to certain alternatives of the invention, the non-volatile non-polar hydrocarbon-based oil is chosen from the oils that can solubilize at least partially the silicone resin, at least partially the silicone polyamide (protocol identical to that of the test described hereinbelow in the description).

Polar Wax(es)

As indicated hereinabove, the composition according to the invention comprises at least one polar wax, hydrocarbon or silicon, of which the melting point is less than or equal to 90° C. Preferably, the composition according to the invention comprises at least two different polar waxes.

The polar wax considered in the framework of this invention is in general a lipophilic compound, which is solid at ambient 25° C. having a reversible solid/liquid change of state, having a melting point in particular greater than or equal to 30° C. and less than or equal to 90° C., more particularly less than or equal to 80° C. and preferably less than or equal to 70° C.

The melting point of a solid fat can be measured using a differential scanning calorimeter (DSC), for example the calorimeter sold under the trade name "DSC Q100" by TA Instruments with the "TA Universal Analysis" software.

According to the invention, the melting temperature corresponds more particularly to the temperature of the most endothermic peak observed in DSC as described in the norm ISO 11357-3; 1999.

The measurement protocol can be as follows:

A sample of solid fat of about 5 mg is placed in a "sealed aluminum capsule" crucible.

When the solid fat is hard (wax), the sample is subjected to a first temperature rise from 20° C. to 120° C., at a heating rate of 2° C./minute, and to 80° C., then left at isotherm of 100° C. for 20 minutes, then is cooled from 120° C. to 0° C. at a cooling rate of 2° C./minute, and finally subjected to a second temperature rise from 0° C. to 20° C. at a heating rate of 2° C./minute.

The value of the melting temperature of the solid fat is the value of the top of the most endothermic peak of the fusion curve observed, representing the variation in the difference in power absorbed as a function of the temperature. In particular, the polar waxes implemented in the composition according to the invention, have a melting temperature greater than 30° C. and better greater than 45° C.

More particularly, the polar wax is chosen from the ester hydrocarbon waxes, alcohol hydrocarbon waxes, silicone waxes, as well as mixtures thereof.

The term "hydrocarbon wax" refers to a wax essentially formed, or consisting, of carbon and hydrogen atoms, and optionally oxygen, nitrogen atoms, and containing no silicon or fluorine. It may contain alcohol, ester, ether, carboxylic acid, amine and/or amide groups.

The term "ester wax" refers according to the invention to a wax that comprises at least one ester function. The ester waxes can furthermore be hydroxylated.

The term "alcohol wax" refers according to the invention to a wax that comprises at least one alcohol function, i.e. that comprises at least one free hydroxyl (OH) group. The additional alcohol wax does not comprise in particular any ester function.

The term "silicon oil" refers to an oil comprising at least one silicon atom and particularly comprising Si—O groups.

Ester Waxes

The following can in particular be used as an ester wax: ester waxes such as those chosen from:

i) the waxes having formula $R_1COOR_2$ wherein $R_1$ and $R_2$ are aliphatic linear, branched or cyclic chains of which the number of atoms varies from 10 to 50, that can contain a heteroatom in particular oxygen, and of which the melting point temperature varies from 30 to 120° C., preferably from 30 to 100° C. In particular it is possible to use as ester wax a $C_{20}$-$C_{40}$ (hydroxystearyloxy)alkyl stearate (with the alkyl group comprising from 20 to 40 carbon atoms), alone or in a mixture or a $C_{20}$-$C_{40}$ alkyl stearate. Such waxes are particular sold under the names "Kester Wax K 82 P®", "Hydroxypolyester K 82 P®", "Kester Wax K 80 P®", or "KESTER WAX K82H" by KOSTER KEUNEN. Mixtures of C14-C18 carboxylic acid esters and of alcohols such as the "Cetyl Ester Wax 814" product of KOSTER KEUNEN, "SP Crodamol MS MBAL", "Crodamol MS PA" from CRODA, "Miraceti" from LASERSON can also be used.

A montanate (octacosanoate) of glycol and of butylene glycol can also be used such as the LICOWAX KPS FLAKES wax (INCI name: glycol montanate) sold by Clariant.

ii) di-(trimethylol-1,1,1 propane) tetrastearate, sold under the name Hest 2T-4S® by HETERENE.

iii) diester waxes of a carboxylic diacide having general formula $R^3$—(—OCO—$R^4$—COO—$R^5$), wherein $R^3$ and $R^5$ are identical or different, preferably identical and is a $C_4$-$C_{30}$ alkyl group (alkyl group comprising from 4 to 30 carbon atoms) and $R^4$ is a $C_4$-$C_{30}$ linear or branched aliphatic group (alkyl group comprising from 4 to 30 carbon atoms) and which can contain or not one or several unsaturations. Preferably, the $C_4$-$C_{30}$ aliphatic group is linear and unsaturated.

iv) the waxes obtained by catalytic hydrogenation of animal or plant oils that in particular have $C_8$-$C_{32}$ linear or branched fat chains, for example such as hydrogenated jojoba oil, hydrogenated sunflower oil, hydrogenated castor oil, hydrogenated coconut oil, as well as the waxes obtained by hydrogenating esterified castor oil with cetyl alcohol, such as those sold under the names Phytowax ricin 16L64® and 22L73® by SOPHIM. Such waxes are described in application FR-A-2792190. As waxes obtained by hydrogenating esterified olive oil with stearyl alcohol, mention can be made of those sold under the name "PHYTOWAX Olive 18 L 57".

v) waxes of animal or plant origin, such as beeswax, synthetic beeswax, carnauba wax, candellila wax, lanolin wax, rice bran wax, Ouricury wax, Alfa wax, berry wax, shellac wax, cork fiber wax, sugarcane wax, Japan wax, sumac wax, montan wax, Orange and Lemon waxes, Bay leaf wax, hydrogenated Jojoba wax, sunflower wax, in particular refined.

vi) Mention can also be made of hydrocarbon, polyoxyalkylene or polyglycerol waxes, natural or synthetic, of animal or plant origin; the number of oxyalkylene patterns ($C_2$-$C_4$) can vary from 2 to 100, the number of glycerol patterns can vary from 1 to 20. As examples, mention can be made of polyoxyethylene beeswax, such as PEG-6 beeswax, PEG-8 beeswax; polyoxyethylene carnauba waxes, such as PEG-12 carnauba; lanolin waxes, hydrogenated or not, polyoxyethene or polyoxypropylene, such as PEG-30 lanolin, PEG-75 lanolin; PPG-5 lanoline wax glyceride; polyglycerole beeswax, in particular polyglyceryl-3 Beewax, the *Acacia Decurrens*/Jojoba/Sunflower Seed Wax/Polyglyceryl-3 Esters mixture, polyglycerol plant waxes such as mimosa, jojoba, sunflower waxes, and mixtures thereof (*Acacia Decurrens*/Jojoba/Sunflower Seed Wax Polyglyceryl-3 Esters.

vii) Waxes corresponding to partial or total esters, preferably total, of a $C_{16}$-$C_{30}$ carboxylic, saturated, possibly hydroxylated, with glycerol. The term total esters means that all of the hydroxyl functions of the glycerol are esterified. As an example, mention can be made of trihydroxystearine (or glyceryl trihydroxystearate), tristearine (or glyceryl tristearate), tribehenin (or glyceryl tribehenate), alone or in a mixture. Among the suitable compounds, mention can be made of glycerol triesters and of 12-hydroxystearic acid or hydrogenated castor oil, such as for example Thixcin R, Thixcin E, sold by Elementis Specialties.

viii) as well as mixtures thereof.

Alcohol Waxes

As for alcohol wax, mention can be made of alcohols, preferably linear, preferably saturated, comprising from 16 to 60 carbon atoms, of which the melting point is between 25° C. and 90° C. As examples of alcohol wax, mention can be made of stearyl alcohol, cetyl alcohol, myristyl alcohol, palm alcohol, behenic alcohol, erucic alcohol, arachidylic alcohol, or mixtures thereof.

Silicone Waxes

As silicone wax, mention can be made for example of mixtures comprising a compound of the C30-45 Alkyldimethylsilyl Polypropylsilsesquioxane type (INCI name), for example the Dow Corning product SW-8005 C30 Resin Wax sold by Dow Corning. Mention can also be made of mixtures comprising a compound of the C30-45 Alkyl Methicone type (INCI name), such as for example the Dow Corning® product AMS-C30 Cosmetic Wax. Mention can also be made of silicone beeswax.

The composition according to the invention comprises a content in polar wax(es) of at least 7% by weight in relation to the total weight of the composition.

Preferably, it comprises a content in polar wax(es) of at least 8% by weight, preferably at least 9% by weight with respect to the total weight of the composition. Preferably it comprises a content in polar wax(es) between 7% and 20%, preferably between 7.5% and 20%, preferably between 8 and 13% by weight in relation to the total weight of the composition.

Additional Non-Polar Hydrocarbon Waxes

The composition can possibly comprise at least one additional wax chosen from non-polar hydrocarbon waxes.

The term "non-polar hydrocarbon wax", in terms of this invention refers to a wax that comprises only carbon or hydrogen atoms in its structure. In other terms, such a wax is free of other atoms, in particular heteroatoms such as for example nitrogen, oxygen, silicon.

For the purposes of illustration of non-polar waxes suitable for the invention, mention can in particular be made of hydrocarbon waxes such as microcrystallin waxes, paraffin waxes, ozokerite, polymethylene waxes, polyethylene waxes, waxes obtained by Fischer-Tropsch synthesis, microwaxes in particular polyethylene.

Preferably, the additional non-polar hydrocarbon wax is chosen from waxes of which the melting point is in particular greater than or equal to 30° C. and less than or equal to 90° C., more particularly less than or equal to 80° C., and preferably less than or equal to 70° C.

If the composition contains any, the content in additional non-polar hydrocarbon wax(es) is such that the total content in wax is less than or equal to 20% by weight with respect to the weight of the composition, preferably less than or equal to 13% by weight with respect to the weight of the composition.

According to a very advantageous embodiment, the content in additional non-polar hydrocarbon wax(es) is such that the weight ratio polar wax(es)/additional non-polar hydrocarbon wax(es) is greater than 1.

Preferably, if it contains any, the content in additional non-polar hydrocarbon wax(es) is between 0 and 5% by weight, with respect to the weight of the composition.

Additional Oils

In accordance with a preferred embodiment of the invention, the composition comprises at least one additional oil chosen volatile or non-volatile silicon oils, volatile or non-volatile hydrocarbon non-polar oils, as well as mixtures thereof.

According to this particularly advantageous embodiment of the invention, the content of additional oil(s) is from 1% to 30% by weight, preferably from 3% to 25% by weight, preferably from 5 to 20% by weight, and even more preferentially from 7% to 20% by weight, with respect to the weight of the composition.

A first embodiment of the invention is represented by a composition comprising at least one additional non-volatile non-polar silicon or hydrocarbon oil, and preferably at least one non-volatile silicon oil, possibly associated with at least one volatile hydrocarbon or silicone oil, or mixtures thereof.

In this case, the content in volatile oil(s) is more particularly between 0.1 and 15% by weight, more particularly between 1 and 10%, by weight, in relation to the weight of the composition.

Preferably, according to this alternative, the weight ratio additional non-volatile oil(s)/volatile oil(s) greater than 1, preferably greater than or equal to 2.

A second embodiment of the invention is represented by a composition that does not contain any additional non-volatile oil, but at least one volatile silicone or hydrocarbon oil, or mixtures thereof.

According to this embodiment, the content in additional volatile oil(s) varies more particularly from 3 to 15% by weight, and preferably between 3 and 8%, by weight, in relation to the weight of the composition.

Preferably, according to this particular embodiment, the weight ratio non-volatile polar oil(s)/additional volatile oil(s) is greater than 1.

Silicone Oils

According to a first preferred alternative of the invention, the continuous fatty phase comprises at least one silicone oil. The latter can be a volatile oil or a non-volatile oil.

The term "silicone oil" refers to an oil containing at least one silicon atom and particularly containing Si—O groups.

Preferably, the composition comprises at least one silicone oil that can solubilize at least partially the silicone resin, at least partially the silicone polyamide.

More particularly, the composition comprises at least one volatile or non-volatile silicone oil, that satisfies the following test:

A mixture of silicone resin and of silicone oil is prepared, in the following proportions: 25 g resin for 75 g of oil; with the resin and the oil not being conveyed or diluted or solubilized before the test. The mixture is made under stirring for 2 hours, at a temperature between 20° C. and the vitreous transition temperature of the compound associated with the oil, here the resin (determination by differential scanning calorimeter—DSC).

It is said that the silicone oil solubilizes at least partially the silicone resin when the viscosity of the silicone oil alone is less than that of the silicone oil and silicone resin mixture, measured at 20° C. and atmospheric pressure (viscosity measurement carried out using a RHEOMAT RM 100 viscometer equipped with a mobile no. 2, 3, or 4, according to the recommendations of the supplier, with the measurement being carried out after 10 minutes of rotation of the mobile within the mixture).

In accordance with a more preferred embodiment, an oil is chosen of which the aforementioned mixture leads to the obtaining of a homogeneous phase without agglomerate, grains or phase dispersed in the other (observation with the unaided eye or with the phase contrast microscope, at ambient temperature (20° C.)).

The same test can be carried out with the silicone polyamide.

Preferably, an oil is used that solubilizes at least partially, both the silicone resin and the silicone polyamide.

Silicone Volatile Oils

The term volatile oil refers to an oil that has a non-zero vapor pressure, at ambient temperature and atmospheric pressure, ranging in particular from 0.13 Pa to 40,000 Pa, in particular ranging to 13,000 Pa, and more particularly ranging to 1,300 Pa.

The volatile silicone oil may be chosen from linear or cyclic silicone oils such as linear or cyclic polydimethylsiloxanes (PDMS) having 3 to 7 silicon atoms.

By way of example of such oils, mention may be made of octyltrimethicone, hexyltrimethicone, decamethylcyclopentasiloxane (cyclopentasiloxane or D5), octamethylcyclotetrasiloxane (cyclotetradimethylsiloxane or D4), dodecamethylcyclo-hexasiloxane (D6), decamethyltetrasiloxane (L4), polydimethysiloxanes such as those sold under the reference DC 200 (1.5 cSt), DC 200 (5 cSt), DC 200 (3 cSt) by Dow Corning, of KF 96 A of Shin Etsu; alone or in mixtures.

Non-Volatile Silicone Oils

Among the non-volatile silicone oils that can be used in this invention, mention can be made for example of non-phenylated non-volatile silicone oils and phenylated non-volatile silicone oils.

The silicone oils that can be used in terms of the invention advantageously have a molecular weight less than or equal to 150,000 g/mol, preferably less than or equal to 100,000 g/mol, and better less than or equal to 10,000 g/mol.

Non-phenylated non-volatile silicone oils

The expression "non-phenylated silicone oil" designates a silicone oil that does not comprise any phenyl substituents.

Examples that are representative of these non-phenylated non-volatile silicone oils that can be mentioned, comprise polydimethylsiloxanes; alkyldimethicones; vinylmethylmethicones.

Note that these non-phenylated non-volatile silicone oils do not contain any patterns of the ethylene oxide, propylene oxide or glycerol type. They are therefore different from the silicone surfactants described hereinabove.

Moreover, the term "dimethicone" (INCI name) corresponds to a polydimethylsiloxane (chemical name).

In particular, these oils can be chosen from the following non-volatile oils:
polydimethylsiloxanes (PDMS),
alkyldimethicones comprising aliphatic groups, in particular alkyl, or alkoxy, which are pendant and/or at the end of the silicone chain; these groups each comprise from 2 to 24 carbon atoms. As an example mention can be made of cetyldimethicone sold under the trade name ABIL WAX 9801 from Evonik Goldschmidt,
polydimethylsiloxanes comprising functional groups such as hydroxyl groups,
substituted polydimethylsiloxane aliphatic groups, in particular $C_2$-$C_{24}$ alkyl, pendant and/or at the end of the silicone chain, and by functional groups such as hydroxyl groups,
mixtures thereof.

Preferably, these non-phenylated non-volatile silicone oils are chosen from polydimethylsiloxanes; alkyldimethicones and also from polydimethylsiloxanes substituted with aliphatic groups, in particular $C_2$-$C_{24}$ alkyl, and functional groups such as hydroxyl groups.

The non-phenylated non-volatile silicone oil may particularly be chosen from silicones having formula (I):

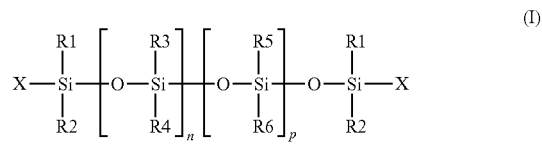

wherein:
$R_1$, $R_2$, $R_5$ and $R_6$ are, together or separately, an alkyl radical containing 1 to 6 carbon atoms,
$R_3$ and $R_4$ are, together or separately, an alkyl radical Containing 1 to 6 carbon atoms or a hydroxyl radical,
X is an alkyl radical containing 1 to 6 carbon atoms, a hydroxyl radical,
n and p are integers chosen in such a way as to have a fluid compound, in particular of which the viscosity at 25° C. is between 8 centistokes (cSt) ($8\times10^{-6}$ m$^2$/s) and 800,000 cSt, advantageously less than 100,000 cSt, and advantageously a mean molar mass by weight less than or equal to 150,000 g/mol, preferably less than or equal to 100,000 g/mol, and better less than or equal to 10,000 g/mol.

As non-volatile non-phenylated silicone oils suitable for the realization of the invention, mention can be made of those for which:
the substituents $R_1$ to $R_6$ and X represent a methyl group, and p and n are such that the viscosity is 60,000 cst, for example the product sold under the name Dow Corning 200 Fluid 60000 CS by Dow Corning, and the product sold under the name Wacker Belsil DM 60000 by Wacker,
the substituents $R_1$ to $R_6$ and X represent a methyl group, and p and n are such that the viscosity is 100 cSt, or 350 cSt, for example the products sold respectively under the names Belsil DM100, Dow Corning 200 Fluid 350 CS, by Dow Corning, and
the substituents $R_1$ to $R_6$ represent a methyl group, the group X represents a hydroxy group, and n and p are such that the viscosity is 700 cSt, for example the product sold under the name Baysilone Fluid T0.7 by Momentive.

Non-Volatile Phenylated Silicone Oils

The expression "phenylated silicone oil" designates a silicone oil that has at least one phenyl substituent.

These non-volatile phenylated silicone oils can be chosen from those that furthermore have at least one dimethicone fragment, or from those that do not have any. Note that the terms "dimethicone fragment" designate a divalent siloxane group of which the silicon atom carried two methyl radicals, with this group not being located at the ends of the molecule. It can be represented by the following formula: —(Si(CH$_3$)$_2$—O)—.

The non-volatile phenylated silicone oil can as such be chosen from:
phenylated silicone oils that have or do not have a dimethicone fragment corresponding to the following formula (I):

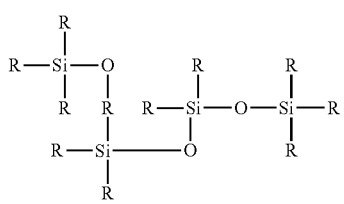

(I)

wherein the R groups, monovalent or divalent, are, independently from one another, a methyl, methylene, phenyl or phenylene, provided that at least one R group is a phenyl.

Preferably, in this formula, the phenylated silicone oil comprises at least three phenyl groups, for example at least four, at least five or at least six.
phenylated silicone oils that have or do not have a dimethicone fragment corresponding to the following formula (2):

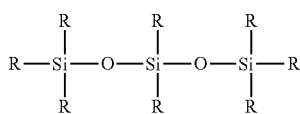

(II)

wherein the R groups are, independently from one another, a methyl or a phenyl, provided that at least one R group is a phenyl.

Preferably, in this formula, the compound of formula (II) comprises at least three phenyl groups, for example at least four or at least five.

Mixtures of the various phenylorganopolysiloxane compounds described hereinabove may be used.

Examples that can be mentioned comprise mixtures of triphenyl-, tetraphenyl-oru pentaphenyl-organopolysiloxanes.

Among the compounds having formula (II), more particular mention can be made of phenylated silicone oils that do not have any dimethicone fragment corresponding to the formula (II) in which at least 4 or at least 5 R radicals are a phenyl radical with the remaining radicals being methyls.

Such non-volatile phenylated silicone oils are preferably trimethylpentaphenyl-trisiloxane, or tetramethyl-tetraphenyl-trisiloxane. They are in particular sold by Dow Corning under the reference PH-1555 HRI or Dow Corning 555 Cosmetic Fluid (chemical name: 1,3,5-trimethyl-1,1,3,5,5-pentaphenyl-trisiloxane; INCI name: trimethyl-pentaphenyltrisiloxane), or tetramethyl-tetraphenyl-trisiloxane sold under the reference Dow Corning 554 Cosmetic Fluid by Dow Corning can also be used.

They correspond in particular to the following formulas (III) and (III'):

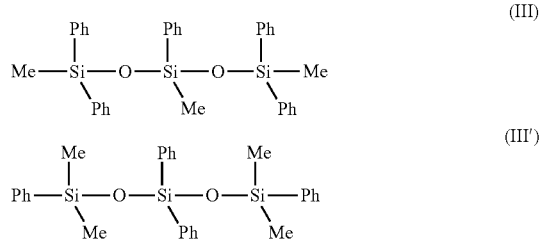

wherein Me represents methyl, Ph represents phenyl.
phenylated silicone oils that at least one dimethicone fragment corresponding to the following formula (IV):

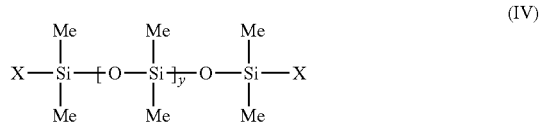

(IV)

wherein Me represents methyl, y is between 1 and 1,000 and X represents —CH$_2$—CH(CH$_3$)(Ph).
phenylated silicone oils corresponding to the formula (V) hereinbelow, and mixtures of the latter:

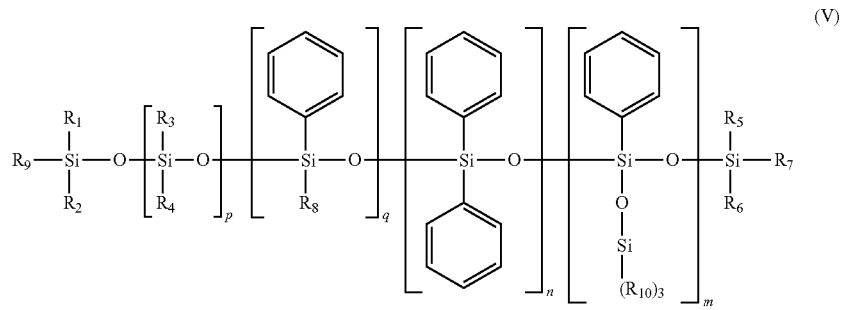

(V)

wherein:
R$_1$ to R$_{10}$, independently of each other, are C$_1$-C$_{30}$ linear, cyclic or branched, saturated or unsaturated hydrocarbon radicals,
m, n, p and q are, independently of each other, integers between 0 and 900, provided that the sum m+n+q is different to 0.

Preferably, the sum m+n+q is between 1 and 100. Advantageously, the sum m+n+p+q is between 1 and 900 and preferably between 1 and 800.

Preferably, q is equal to 0.

More particularly, $R_1$ to $R_{10}$, independently of one other, are a $C_1$-$C_{30}$ linear or branched, saturated or unsaturated, preferably saturated, hydrocarbon radical, and in particular a $C_1$-$C_{20}$ hydrocarbon radical, preferably saturated, in particular $C_1$-$C_{18}$, or a $C_6$-$C_{14}$ aryl radical and in particular $C_{10}$-$C_{13}$, monocyclic or polycyclic, or an aralkyl radical preferably of which the alkyl portion is $C_1$-$C_3$.

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical. $R_1$ to $R_{10}$ may in particular be identical and, moreover, may be a methyl radical.

As particular embodiments of the formula (V), mention can be made of:
- phenylated silicone oils that have or do not have at least one dimethicone fragment corresponding to the formula (VI) hereinbelow, and mixtures of the latter:

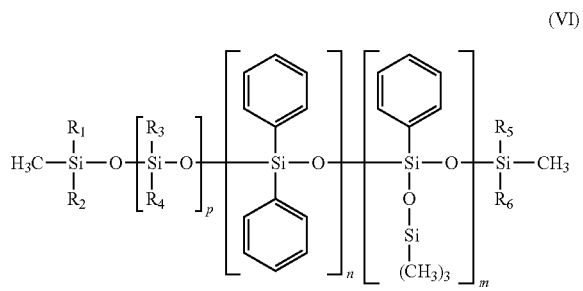

wherein:
- $R_1$ to $R_6$, independently of one other, are $C_1$-$C_{30}$ saturated or unsaturated, linear, cyclic or branched hydrocarbon radicals, an aryl radical, preferably $C_6$-$C_{14}$, or an aralkyl radical of which the alkyl portion is $C_1$-$C_3$).
- m, n and p are, independently of one other, integers between 0 and 1000 and more preferably between 0 and 100, provided that the sum n+m is between 1 and 1000 and more preferably between 1 and 100.

Preferably, $R_1$ to $R_6$, independently of one other, are a hydrocarbon radical, preferably alkyl, $C_1$-$C_{20}$, in particular $C_1$-$C_{18}$, or a $C_6$-$C_{14}$ monocyclic aryl radical (preferably $C_6$) or polycyclic and in particular $C_{10}$-$C_{13}$, or an aralkyl radical (preferably the aryl portion is $C_6$; the alkyl portion is $C_1$-$C_3$).

Preferably, $R_1$ to $R_{10}$ may each represent a methyl, ethyl, propyl, butyl, isopropyl, decyl, dodecyl or octadecyl radical, or alternatively a phenyl, tolyl, benzyl or phenethyl radical.

$R_1$ to $R_6$ may in particular be identical and, moreover, may be a methyl radical. Preferably, m=1 or 2 or 3, and/or n=0 and/or p=0 or 1 can be applied, in formula (VI).

According to a particular embodiment, the non-volatile phenylated silicone oil is chosen from the phenylated silicone oils that have at least one dimethicone fragment.

Preferable, such oils correspond to compounds having the formula (VI) wherein:
- m=0 and n and p are, independently of each other, integers between 1 and 100.

Preferably $R_1$ to $R_6$ are methyl radicals.

According to this embodiment, the silicone oil is preferably chosen from a diphenyldimethicone such as KF-54 from Shin Etsu (400 cSt), KF54HV from Shin Etsu (5000 cSt), KF-50-300CS from Shin Etsu (300 cSt), KF-53 from Shin Etsu (175 cSt), KF-50-100CS from Shin Etsu (100 cSt).

p is between 1 and 1000, the sum n+m is between 1 and 1000, and n=0.

These phenylated silicone oils that have or do not have at least one dimethicone fragment corresponding more particularly to the formula (VII) hereinbelow:

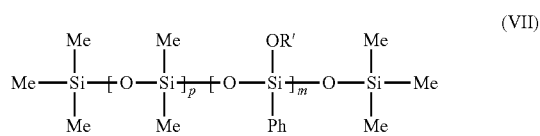

wherein Me is methyl and Ph is phenyl, OR' is a —OSiMe$_3$ group and p is 0 or is between 1 and 1000, and m is between 1 and 1000. In particular, m and p are such that the compound (VII) is a non-volatile oil.

According to a first embodiment of non-volatile phenylated silicone that has at least one dimethicone fragment, p is between 1 and 1000. m is more particularly such that the compound (VII) is a non-volatile oil. For example, trimethylsiloxyphenyldimethicone can be used, sold in particular under the reference Belsil PDM 1000 by Wacker.

According to a second embodiment of non-volatile phenylated silicone that do not have any dimethicone fragment, p is equal to 0. m is between 1 and 1000, and in particular, is such that the compound (VII) is a non-volatile oil.

For example, phenyltrimethicone can be used, sold in particular under the reference Dow Corning 556 Cosmetic Grade Fluid (DC556).
- phenylated non-volatile silicone oils that do not have any dimethicone fragment corresponding to the formula (VIII) hereinbelow, and mixtures of the latter:

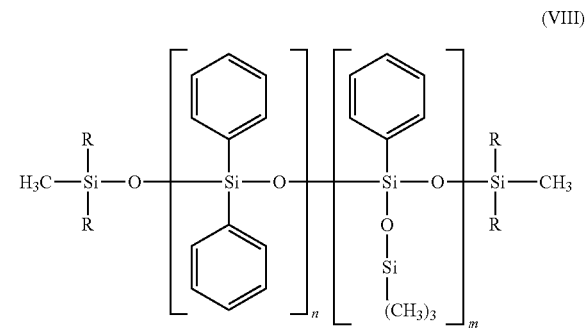

wherein:
- R, independently of each other, are $C_1$-$C_{30}$ saturated or unsaturated, linear, cyclic or branched hydrocarbon radicals, preferably R is a $C_1$-$C_{30}$ alkyl radical, an aryl radical, preferably $C_6$-$C_{14}$, or an aralkyl radical of which the alkyl portion is $C_1$-$C_3$.
- m and n are, independently of one other, integers between 0 and 100, provided that the sum n+m is between 1 and 100.

More preferably, R, independently of each other, are a $C_1$-$C_{30}$ saturated or unsaturated, linear or branched, preferably saturated, hydrocarbon radical, and in particular a hydrocarbon radical, preferably saturated, $C_1$-$C_{20}$, in particular $C_1$-$C_{18}$ and more particularly $C_4$-$C_{10}$, a $C_6$-$C_{14}$ monocyclic or polycyclic aryl radical and in particular $C_{10}$-$C_{13}$, or an aralkyl radical preferably the aryl portion is $C_6$ and the alkyl portion is $C_1$-$C_3$.

Preferably, Rs may each represent a methyl, ethyl, propyl, butyl, isopropyl, decyl, dodecyl or octadecyl radical, or alternatively a phenyl, tolyl, benzyl or phenethyl radical.

The Rs may in particular be identical and, moreover, may be a methyl radical.

Preferably, m=1 or 2 or 3, and/or n=0 and/or p=0 or 1 can be applied, in formula (VIII).

According to a preferred embodiment, n is an integer between 0 and 100 and m is an integer between 1 and 100, provided that the sum n+m is between 1 and 100, in the formula (VIII). Preferably, R is a methyl radical.

According to one embodiment, a phenylated silicone oil having formula (VIII) having a viscosity at 25° C. between 5 and 1500 mm²/s (i.e., from 5 to 1500 cSt), and preferably having a viscosity between 5 and 1000 mm²/s (i.e. 5 to 1000 cSt) can be used.

According to this embodiment, the non-volatile phenylated silicone oil is preferably chosen from phenyltrimethicones (when n=0) such as DC556 from Dow Corning (22.5 cSt), or from diphenylsiloxyphenyltrimethicone oil (when m and n are between 1 and 100) such as KF56 A from Shin Etsu, Silbione oil 70663V30 from Rhône-Poulenc (28 cSt). The values between brackets represent the viscosities at 25° C.

phenylated silicone oils that have or do not have at least one dimethicone fragment corresponding to the following formula, and mixtures of the latter:

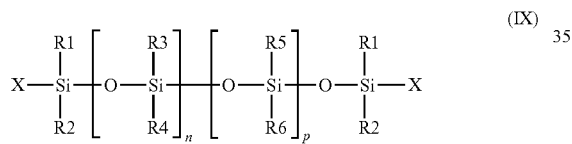

(IX)

wherein:

$R_1$, $R_2$, $R_5$ and $R_6$ are, identical or not, an alkyl radical containing 1 to 6 carbon atoms, $R_3$ and $R_4$ are, identical or not, an alkyl radical containing 1 to 6 carbon atoms or an aryl radical (preferably $C_6$-$C_{14}$), with the condition that at least one of $R_3$ and $R_4$ is a phenyl radical, X is an alkyl radical containing 1 to 6 carbon atoms, a hydroxyl radical or a vinyl radical, n and p being an integer greater than or equal to 1, chosen in such w way as to confer to the oil a mean molar mass by weight preferably less than 150,000 g/mole and more preferably less than 100,000 g/mole.

and a mixture of the latter.

In accordance with a more suitable embodiment of the invention, the composition comprises at least one silicone oil, and preferably at least one non-volatile silicone oil.

More particularly, the non-volatile silicone oils are chosen from the phenylated non-volatile silicone oils and more preferably from non-volatile silicone oils having formula (VI) and more particularly having formulas (VII) and (VIII). Preferably, the composition comprises at least one phenylated non-volatile silicone oil chosen from phenyl trimethicone, diphenylsiloxyphenyltrimethicone, as well as mixtures thereof.

Non-Polar Hydrocarbon Oils
Non-Polar Non-Volatile Hydrocarbon Oils

Non-polar non-volatile hydrocarbon oils are more particularly chosen from compounds that comprise only carbon and hydrogen atoms.

Said oils, linear or branched, can be of mineral or synthetic origin such as for example:
paraffin oil or derivatives thereof,
squalane,
isoeicosane,
naphthalene oil,
polybutenes, hydrogenated or not, such as for example INDOPOL H-100, INDOPOL H-300, INDOPOL H-1500 sold or manufactured by AMOCO,
polyisobutenes, hydrogenated polyisobutenes such as for example Parléam® sold by NIPPON OIL FATS, PANALANE H-300 E sold by AMOCO, VISEAL 20000 sold by SYNTEAL, REWOPAL PIB 1000 sold by WITCO, or PARLEAM LITE sold by NOF Corporation,
decene/butene copolymers, polybutene/polyisobutene copolymers particularly Indopol L-14,
polydecenes and hydrogenated polydecenes such as for example PURESYN 10, PURESYN 150 or PURESYN 6 sold by EXXONMOBIL CHEMICAL),
and mixtures thereof.

Non-Polar Volatile Hydrocarbon Oils

The non-polar volatile hydrocarbon oils are preferably chosen from non-polar hydrocarbon oils and in particular can be chosen from volatile hydrocarbon oils that have from 8 to 16 carbon atoms and mixtures thereof, and in particular:
$C_8$-$C_{16}$ branched alkanes such as iso-alkanes (also called isoparaffins) in $C_8$-$C_{16}$, isododecane, isodecane, isohexadecane, and for example the oils sold under the trade names Isopars or Permetyls,
linear alkanes, for, example such as n-dodecane (C12) and n-tetradecane (C14) sold by Sasol respectively under the references PARAFOL 12-97 and PARAFOL 14-97, as well as mixtures thereof, the undecane-tridecane mixture (Cetiol UT), the mixtures of n-undecane (C11) and of n-tridecane (C13) obtained in examples 1 and 2 of application WO2008/155059 of Cognis, and mixtures thereof.

Pasty Compounds (or Pasty Fat)

The composition according to the invention may also comprise at least a pasty compound at 23° C., hydrocarbon or silicon.

For the purposes of the invention, the term "pasty fat" refers to a lipophilic fat compound having a reversible solid/liquid change of state, having in the solid state, an anisotropic crystalline organization, and comprising at a temperature of 23° C. a liquid fraction and a solid fraction.

In other words, the initial melting point of the pasty compound may be less than 23° C. The liquid fraction of the pasty compound measured at 23° C. may represent 9 to 97% by weight of the compound. This liquid fraction at 23° C. preferably represents between 15 and 85%, more preferably between 40 and 85% by weight.

The melting point of a solid fat can be measured using a differential scanning calorimeter (DSC), for example the calorimeter sold under the trade name "DSC Q100" by TA Instruments with the "TA Universal Analysis" software, according to the protocol defined hereinabove.

According to the invention, the melting temperature corresponds to the temperature of the most endothermic peak observed in DSC as described in the norm ISO 11357-3; 1999.

The measurement protocol is as follows:

A sample of solid fat of about 5 mg is placed in a "sealed aluminum capsule" crucible.

The sample is subjected to a first temperature rise from 20° C. to 80° C., at a heating rate of 2° C./minute to 80° C., then left at isotherm of 80° C. for 20 minutes, then is cooled from 80° C. to −80° C. at a cooling rate of 2° C./minute, and finally subjected to a second temperature rise from −80° C. to 20° C. at a heating rate of 2° C./minute.

The value of the melting temperature of the solid fat is the value of the top of the most endothermic peak of the fusion curve observed, representing the variation in the difference in power absorbed as a function of the temperature.

The liquid fraction by weight of the pasty compound at 23° C. is more particularly equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is said to be in the solid state when the entire mass thereof is in solid crystalline form. The pasty compound is said to be in the liquid state when the entire mass thereof is in liquid form.

The enthalpy of fusion of the pasty compound is in particular equal to the area under the curve of the thermogram obtained using a differential scanning calorimeter. The enthalpy of fusion of the pasty compound is the quantity of energy required to change the compound from the solid state to the liquid state. It is expressed in J/g.

The enthalpy of fusion consumed at 23° C. is the quantity of energy required by the sample to change from the solid state to the state presented at 23° C. consisting of a liquid fraction and a solid fraction.

The pasty compound(s) can be in particular chosen from synthetic pasty compounds and fatty substances of plant origin. The pasty compound(s) can be hydrocarbon or silicone.

The pasty compound(s) can be in particular chosen from:
lanolin and its derivatives, such as lanolin alcohol, oxyethylenated lanolins, acetylated lanolin, lanolin esters such as isopropyl lanolate, oxypropylenated lanolins;
vaseline (also called petrolatum),
polyol ethers chosen from C2-C4 pentaerythritol and polyalkylene glycol ethers, fatty alcohol and sugar ethers, and mixtures thereof. For example, mention can be lade of pentaerythritol and polyethylene glycol ether comprising 5 oxyethylene patterns (5 OE) (CTFA name: PEG-5 Pentaerythrityl Ether), pentaerythritol and polypropylene glycol ether comprising 5 oxypropylene units (5 OP) (CTFA name: PPG-5 Pentaerythrityl Ether), and the mixtures thereof and more specifically the mixture of PEG-5 Pentaerythrityl Ether, PPG-5 Pentaerythrityl Ether and soybean oil, sold under the name "Lanolide" VEVY, wherein the ratio of the constituents by weight is 46:46:8:46% PEG-5 Pentaerythrityl Ether, 46% PPG-5 Pentaerythrityl Ether and 8% soybean,
optionally polymeric silicone compounds,
optionally polymeric fluorinated compounds,
vinyl polymers, in particular:
olefin homopolymers and copolymers;
hydrogenated diene homopolymers and copolymers;
branched oligomers, alkyl (meth)acrylate homo or copolymers preferably having a C8-C30 alkyl group,
ester homo and copolymer oligomers, having C8-C30 alkyl groups, and
ester homo and copolymer oligomers, having C8-C30 alkyl groups
polyethers derived from polyetherification between one or a plurality of C2-C100, preferably C2-C50, diols. Of the liposoluble polyethers, ethylene-oxide and/or propylene-oxide copolymers with C6-C30 long-chain alkylene-oxides are particularly considered, more preferably such that the weight ratio of ethylene-oxide and/or propylene-oxide with alkylene-oxides in the copolymer is 5:95 to 70:30. In this family, particular mention may be made of copolymers such as long-chain alkylene-oxides arranged in blocks having a mean molecular weight of 1000 to 10000, for example a polyoxyethylene/polydodecyl glycol block copolymer such as the dodecanediol (22 mol) and polyethylene glycol (45 EO) ethers marketed under the brand ELFACOS ST9 by AKZO NOBEL.
esters and polyesters. Among the esters, particular consideration is given to:
oligomer glycerol esters, especially the esters of diglycerol, with monocarboxylic acids, possibly hydroxylated, linear or branched, saturated or not, preferably saturated, C6-C20, and/or dicarboxylic acids, linear or branched, saturated or not, preferably saturated, C6-C10, in particular condensates of adipic acid and glycerol, for which a portion of the hydroxyl groups of the glycerols have reacted with a mixture of fatty acids, such as stearic acid, capric acid, stearic acid, isostearic acid and 12-hydroxystearic acid, such as for example bis-diglyceryl polyacyladipate-2 sold under the reference SOFTISAN® 649 by Sasol,
homopolymers of vinyl ester having C8-C30 alkyl groups, such as polyvinyl laurate (in particular sold under the reference Mexomère PP by Chimex),
arachidyl propionate sold under the brand Waxenol 801 by ALZO,
phytosterol esters,
triglycerides of fatty acids and their derivatives, in particular triglycerides of fatty acids, saturated or not, linear or branched, possibly mono or poly hydroxylated, C6-C30, more particularly C8-C18, possibly hydrogenated (totally or partially); with for example Softisan 100® sold by Sasol,
pentaerythritol esters,
aliphatic esters derived from the esterification of an aliphatic hydroxycarboxylic acid with an aliphatic carboxylic acid. More particularly, the aliphatic carboxylic acid is $C_4$-$C_{30}$, preferably $C_8$-$C_{30}$. It is preferably chosen from hexanoic heptanoic, octanoic, 2-ethylhexanoic, nonanoic, decanoic, undecanoic, dodecanoic, tridecanoic, tetradecanoic, pentadecanoic, hexadecanoic, hexyldecanoic, heptadecanoic, octadecanoic, isostearic, nonadecanoic, eicosanoic, isoarachidique, octyldodecanoic, heneicosanoic and docosanoic acids, and mixtures thereof. The aliphatic carboxylic acid is preferably branched. The hydroxycarboxylic acid ester is advantageously derived from a C2-C40 hydroxylated carboxylic acid, preferably C10-C34, and more preferably C12-C28; with the number of hydroxyl groups being between 1 and 20, more particularly between 1 and 10, preferably between 1 and 6.

Said hydroxycarboxylic acid esters are preferably chosen from:
a) total or partial saturated, linear and monohydroxylated aliphatic monocarboxylic acid esters;
b) total or partial saturated, monohydroxylated aliphatic monocarboxylic acid esters;

c) total or partial saturated, polyhydroxylated aliphatic monocarboxylic acid esters;
d) total or partial saturated, polyhydroxylated aliphatic polycarboxylic acid esters;
e) partial or total $C_2$-$C_{16}$ aliphatic polyol esters with a mono or polyhydroxylated mono or polycarboxylic aliphatic acid
f) mixtures thereof.
  dimer diol and dimer diacid esters, optionally esterified on the alcohol or free acid function(s) thereof by acid or alcohol radicals, in particular dilinoleic dimer esters; such esters may particularly be chosen from esters having the following INCI classification: bis-behenyl/isostearyl/phytosteryl dimerdilinoleyl dimerdilinoleate (Plandool G), phytosteryl/isosteryl/cetyl/stearyl/behenyl dimerdilinoleate (Plandool H or Plandool S) mixtures thereof,
  hydrogenated rosin esters (Lusplan DD-DHR or DD-DHR from Nippon Fine Chemical)
  butters of plant origin, such as mango butter, such as the one sold under the reference Lipex 203 by AARHUSKARLSHAMN, shea butter, in particular the one of which the INCI name is Butyrospermum Parkii Butter, such as the one sold under the reference Sheasoft® by AARHUSKARLSHAMN, cupuacu butter (Rain forest RF3410 from Beraca Sabara), murumuru butter (RAIN FOREST RF3710 from Beraca Sabara), cocoa butter, babassu butter such as the one sold under the name Cropure Babassu SS-(LK) by Croda, as well as orange wax such as, for example, the one sold under the reference Orange Peel Wax by Koster Keunen,
  totally or partially hydrogenated plant oils, such as for example hydrogenated soybean oil, hydrogenated coconut oil, hydrogenated rapeseed oil, mixtures of hydrogenated plant oils such as the mixture of hydrogenated plant oil of soybean, coconut, palm and rapeseed, for example the mixture sold under the reference Akogel® by AARHUSKARLSHAMN (INCI name Hydrogenated Vegetable Oil), trans isomerized partially hydrogenated jojoba oil manufactured or sold by Desert Whale under the commercial reference Iso-Jojoba-50®, partially hydrogenated olive oil such as, for example, the compound sold under the reference Beurrolive by Soliance,
  hydrogenated castor oil esters, such as dimer dilinoleate hydrogenated castor oil for example RISOCAST-DA-L sold by KOKYU ALCOHOL KOGYO, hydrogenated castor oil isostearate for example SALACOS HCIS (V-L) sold by NISSHIN OIL,
  and mixtures thereof.

Preferably, the pasty compound or compounds suitable for the implementation of the invention, is (are) chosen from hydrocarbon compounds, in particular chosen from vaseline, polyol ethers, vinyl polymers, liposoluble polyethers resulting from the polyetherification between one or a plurality of C2-C50 diols, esters and polyesters, butters of plant origin, totally or partially hydrogenated plant oils, and mixtures thereof.

In accordance with a more preferred embodiment of the invention, the pasty compound or compounds are chosen from
  vaseline;
  C2-C4 pentaerythritol and polyalkylene glycol ethers;
  fatty alcohol and sugar ethers;
  ethylene-oxide and/or propylene-oxide copolymers with C6-C30 long-chain alkylene-oxides;
  oligomer glycerol esters, especially the esters of diglycerol, with monocarboxylic acids, possibly hydroxylated, linear or branched, saturated or not, preferably saturated, C6-C20, and/or dicarboxylic acids, linear or branched, saturated or not, preferably saturated, C6-C10; in particular BIS-DIGLYCERYL POLYACYLADIPATE-2 (INCI name), homopolymers of vinyl ester having C8-C30 alkyl groups;
  arachidyl propionate;
  triglycerides of fatty acids, saturated or not, linear or branched, possibly mono or poly hydroxylated, C6-C30, more particularly C8-C18, possibly hydrogenated;
  pentaerythritol esters;
  non-crosslinked esters obtained by condensation of a $C_4$-$C_{50}$ linear or branched di- or poly-carboxylic acid and of a $C_2$-$C_{50}$ diol or polyol, aliphatic esters obtained by the reaction of a hydroxycarboxylic acid ester and of an aliphatic carboxylic acid; advantageously the carboxylic acid is C4-C30,
  dimer diol and dimer diacid esters, such as dilinoleic dimer esters;
  butters of plant origin,
  partially hydrogenated plant oils,
  and mixtures thereof.

According to an embodiment, the composition comprises less than 10% by weight, preferably less than 7%, better less than 5%, and even better less than 3% by pasty fat weight, with respect to the total weight of the composition.

Dispersed Aqueous Phase

The composition according to the invention comprises an aqueous medium, constituting an aqueous phase, which forms the dispersed phase of the composition. The composition according to the invention is indeed a water-in-oil emulsion.

The aqueous phase can be comprised primarily of water; it can also comprise a mixture of water and water-miscible solvent (miscibility in water greater than 50% by weight at 25° C.) such as lower monoalcohols having from 1 to 5 carbon atoms such as ethanol, isopropanol, glycols having from 2 to 8 carbon atoms such as propylene glycol, ethylene glycol, 1,3-butylene glycol, dipropylene glycol, and mixtures thereof.

The composition preferably comprises a content in water that represents at least 7% by weight, preferably a content ranging from 7% to 40% by weight, with respect to the total weight of the composition. Advantageously, the water of the aqueous phase is present in a quantity between 7% and 30% by weight, preferably between 10% and 30% by weight, preferably between 15 and 30% by weight in relation to the total weight of the composition.

According to an embodiment, the composition can comprise at least 60% by water weight, preferably at least 70% by weight, and in particular at least 75% by weight, with respect to the total weight of the aqueous phase.

The composition according to the invention can comprise, in addition to the compounds described hereinabove, water-in-oil surfactants, pasty compounds, oils (silicone and/or non-volatile silicone), aqueous phase thickeners and mixtures thereof. It is understood that the quantity in these annexed compounds can be adjusted by those skilled in the art in such a way as to not bear prejudice to the effect sought in the framework of this invention.

Water-in-Oil Surfactants

The compositions of the invention can comprise surfactant agents of the water-in-oil type. Preferably, the surfactant present in an HLB (hydrophilic/lipophilic balance) less than or equal to 8, more particularly less than or equal to 7, preferably between 1 and 6. Preferably, it is nonionic. The HLB value as per GRIFFIN is defined in J. Soc. Cosm. Chem. 1954 (volume 5), pages 249-256.

Preferably, the surfactant or surfactants are chosen from silicone non-ionic surfactants, from hydrocarbon non-ionic surfactants, or from mixtures thereof.

Silicone Surfactants

With regards to silicone surfactants, mention can be made of alkyl or alkoxy dimethicone copolyols with pendant alkyl or alkoxy chain or silicone backbone-end having for example from 6 to 22 carbon atoms; dimethicone copolyols, which are more particularly oxypropylene and/or oxyethylene polydimethyl methyl siloxanes, as well as cross-linked solid elastomeric organopolysiloxanes that comprise at least one oxyalkylene group, and mixtures thereof.

As an example of alkyl or alkoxy dimethicone copolyols, mention can be made of compounds having the following formula (I):

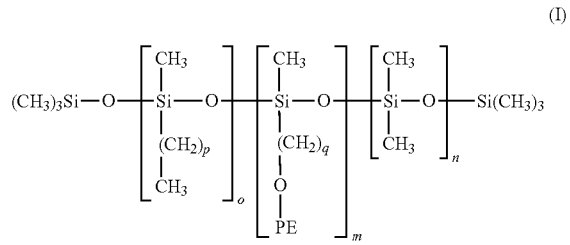

wherein:
PE is $(-C_2H_4O)_x-(C_3H_6O)_y-$R, R being chosen from a hydrogen atom and an alkyl radical from 1 to 4 carbon atoms, x ranging from 0 to 100 and y ranging from 0 to 80, x and y not being simultaneously 0; preferably R is a hydrogen atom;
m varies from 1 to 40; preferably from 1 to 10;
n varies from 10 to 200; preferably from 10 to 100;
o varies from 1 to 100; preferably from 1 to 30;
p varies from 5 to 21, more particularly from 7 to 21;
q varies from 0 to 4, from 1 to 3.

As examples of dimethicone copolyols, those corresponding more particularly to the following formula (II) can be used:

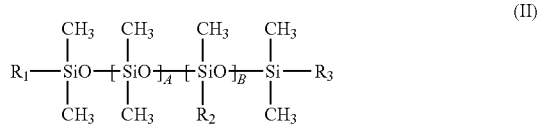

wherein:
$R_1$, $R_2$, $R_3$, independently of each other, are a $C_1$-$C_6$ alkyl radical or a $-(CH_2)_x-(OCH_2CH_2)_y-(OCH_2CH_2CH_2)_z-OR_4$ radical, at least one radical $R_1$, $R_2$ or $R_3$ not being an alkyl radical; $R_4$ being a hydrogen, a $C_1$-$C_3$ alkyl radical or a $C_2$-$C_4$ acyl radical;
A is an integer varying from 0 to 200;
B is an integer varying from 0 to 50; provided that A and B are not equal to zero at the same time;
x is an integer varying from 1 to 6;
y is an integer varying from 1 to 30; and
z is an integer varying from 0 to 30, preferably from 0 to 20.

Among the particularly preferred silicone surfactants, mention can be made of:
dimethicone copolyols such as for example those sold under the names KF-6015 (PEG-3 dimethicone), KF-6016 (PEG-9 methyl ether dimethicone), KF-6017 (PEG-10 dimethicone), KF-6028 (PEG-9 polydimethylsiloxyethyl dimethicone), KF-6050 L (PEG/PPG 18/18 dimethicone in cyclopentasiloxane), by Shin-Etsu; the dimethicone copolyols sold under the names Dow Corning 3225C® (PEG/PPG-18/18 DIMETHICONE in a mixture of cyclotetrasiloxane and cyclopentasiloxane), DC 5225 C Formulation Aid (PEG/PPG-18/18 dimethicone in cyclopentasiloxane); or the product sold under the name SF 1528 GE (mixture of PEG/PPG-20/15 Dimethicone and cyclopentasiloxane) by Momentive Performance Materials.

Alkyl-dimethicone copolyols can also be used such as Lauryl PEG/PPG-18/18 Methicone (which is more particularly an alkoxyl derivative of Lauryl Methicone containing on the average 18 moles of ethylene oxide and 18 moles of propylene oxide, sold under the name "Dow Corning 5200 Formulation Aid" by Dow Corning; cetyl PEG/PPG-10/1 Dimethicone (which is more particularly a copolymer of Cetyl Dimethicone and an alkoxyl derivative of dimethicone containing on the average 10 moles of ethylene oxide and 1 mole of propylene oxide) such as the product sold under the name Abil EM 90 by Evonik Goldschmidt as well as the mixture of cetyl PEG/PPG-10/1 Dimethicone, of polyglycerol isostearate (4 moles) and hexyl laurate sold under the name ABIL WE 09 by Evonik Goldschmidt.

It is also possible to mention, as emulsion surfactants, in particular for water-in-oil emulsions, cross-linked solid elastomeric organopolysiloxanes comprising at least one oxyalkylene group, such as those obtained according to the operating procedure in examples 3, 4 and 8 of document U.S. Pat. No. 5,412,004 and the examples of document U.S. Pat. No. 5,811,487, particularly the product of example 3 (example of synthesis) of the U.S. Pat. No. 5,412,004 and such as that sold under the reference KSG 21 by Shin Etsu.

Preferably, the composition comprises as silicone surfactant(s), C8-C22 alkyl dimethicone copolyol such as cetyl dimethicone copolyol, in particular for which the INCI name is CETYL PEG/PPG-10/1 DIMETHICONE, dimethicone copolyols such as for example PEG-10 dimethicone, PEG/PPG 18/18 dimethicone, as well as mixtures thereof. A mixture of cetyl dimethicone copolyol with polyglyceryl-4-isostearate and hexylaurate can also be used, such as the product sold under the name Abil WE-09 by Evonik Goldschmidt (the INCI name is polyglyceryl-4-isostearate (and) hexylaurate (and) cetyl PEG/PPG-10/1 dimethicone).

Hydrocarbon Surfactants

Non-ionic surfactants can be chosen in particular from alkyl($C_8$-$C_{30}$) ethers of poly(ethylene oxide), alkyl($C_8$-$C_{30}$)— and polyalkyl($C_8$-$C_{30}$)— esters of ethylene oxide, of propylene, of poly(ethylene oxide) or of poly(propylene oxide); fatty acid polyesters, preferably polyhydroxylated, $C_{12}$-$C_{20}$, polyoxyalkylenated, having from 4 to 50 moles of ethylene oxide; alkyl- and polyalkyl-esters of sorbitan; alkyl- and polyalkyl-esters of (poly)glycerol and mixtures thereof.

As alkyl($C_8$-$C_{30}$)— ethers of poly(ethylene oxide), preference is given to the use of those that have a number of ethylene oxide (EO) patterns ranging from 2 to 4. As examples, particular mention can be made of laureth-2; steareth-2, oleth-2; oleth-3; ceteth-2; ceteareth-3.

As alkyl($C_8$-$C_{30}$)— and polyalkyl($C_8$-$C_{30}$)— esters of ethylene oxide, of propylene, of poly(ethylene oxide) or of poly(propylene oxide), preference is given to the use of those that have a number of ethylene oxide (EO) patterns ranging from 1 to 5, with for example glycol distearate, glycol stearate, PEG-2 oleate; EPG-3 oleate; PEG-4 dilaurate, propylene glycol isostearate; PEG-2.5 castor oil; PEG-3 castor oil.

As other surfactants that can be used, mention can be made of $C_{12}$-$C_{20}$ fatty acid polyesters, preferably polyhydroxylated, polyoxyalkylenated, having from 4 to 50 moles of ethylene oxide, that have water-in-oil emulsifying properties. In particular, these polymers are sequenced polymers, preferably with an ABA structure, comprising poly(hydroxyl ester) sequences and polyethyleneglycol sequences. The fatty acid of said emulsifying polymer such as defined hereinabove has preferably from 14 to 18 carbon atoms. The esters can in particular be chosen from olates, palmitates or stearates. The polyethyleneglycol sequences of said emulsifying polymer such as defined hereinabove preferably have from 20 to 40 moles of ethylene oxide. A polymer surfactant that is particularly suitable for the realization of compositions of the invention is di-polyhydroxystearate of polyethylene glycol with 30 EO sold under the trade name Arlacel P 135 by Croda.

As alkyl($C_8$-$C_{30}$)—and polyalkyl($C_8$-$C_{30}$)— esters of sorbitan, particular mention can be made of sorbitan trioleate, sorbitan sesquioleate, sorbitan oleate, sorbitan palmitate; sorbitan stearate, sorbitan isostearate, mixtures of sorbitan stearate and of sucrose cocoate or sorbitan and glycerol isostearate (Arlacel 986 sold by Croda), and mixtures thereof.

As alkyl($C_8$-$C_{30}$)—and polyalkyl($C_8$-$C_{30}$)— esters of (poly)glycerol, preference is given to the use of those that have a number of glycerol patterns ranging from 1 to 4. Mention can be made for example of polyglyceryl-4 isostearate (Isolan GI 34 sold by Evonik Goldschmidt); polyglyceryl-3 diisostearate (LAMEFORM TGI sold by Cognis), glyceryl stearate, glyceryl laurate, alone or in mixtures.

According to a particularly preferred embodiment, the composition comprises at least one silicone non-ionic surfactant.

Advantageously, the silicone surfactant or surfactants are chosen from dimethicone copolyols, alkyl dimethicone copolyols described hereinabove, in particular alkyl $C_8$-$C_{22}$ dimethicone copolyols in particular having formula (I), alone or in mixtures.

According to a particular embodiment of the invention, the composition also comprises at least one hydrocarbon non-ionic surfactant, very particularly alkyl- and polyalkylesters of (poly)glycerol and/or of sorbitan, and preferably polyglyceryl-3 diisostearate, polyglyceryl-4 isostearate, sorbitan isostearate or sorbitan and glycerol isostearate.

The surfactant or surfactants may be present in the composition, in a content ranging from 0.1% to 20% by weight, and preferably from 0.5% to 15%, preferably from 1 to 10% by weight, relative to the total weight of the composition.

Hydrophilic Thickeners

The composition according to the invention can comprise at least one hydrophilic thickening polymer (also called aqueous phase thickening polymer).

Preferably, the composition is such that the hydrophilic thickening polymer is present in a content ranging from 0.02 to 10% by weight, relative to the total weight of the composition, preferably from 0.05 to 7% by weight, more preferably from 0.1 to 5% by weight, relative to the total weight of the composition.

More particularly, this thickening polymer can be chosen from:
homo- or copolymers of acrylic or methacrylic acid or the salts thereof and the esters thereof and in particular the products sold under the names VERSICOL F or VERSICOL K by ALLIED COLLOID, UTRAHOLD 8 by CIBA-GEIGY, polyacrylic acids of the SYNTHALEN K type, and the salts, in particular sodium, of polyacrylic acid (with the INCI name of sodium acrylate copolymer) and more particularly a cross-linked sodium polyacrylate (with the INCI name of sodium acrylate copolymer (and) caprylic/capric triglyceride) sold under the name LUVIGEL EM,
acrylic and acrylamide acid copolymers such as those sold in the form of their sodium salt under the names RETEN by HERCULES, sodium polymethacrylate sold under the name DARVAN N° 7 by VANDERBILT, the sodium salts of polyhydroxycarboxylic acids sold under the name HYDAGEN F by HENKEL,
polyacrylic acid/alkyl acrylates copolymers, preferably carboxyvinyl polymers modified or not, according to this invention, the acrylate/C10-C30-alkylacrylate INCI name Acrylates/C10-30 Alkyl acrylate Crosspolymer) copolymers are very particularly preferred such as the products sold by Lubrizol under the trade names PEMULEN TR1, PEMULEN TR2, CARBOPOL 1382, CARBOPOL EDT 2020 and more preferably PEMULEN TR-2,
homopolymers and copolymers with an acrylamido propane sulfonic acid base, such as for example:
polyacrylamidomethyl propane sulfonic acid partially neutralized with ammonia and highly cross-linked, sold in particular by CLARIANT, for example under the name HOSTACERIN AMPS
copolymers of acrylamidomethyl/acrylamide propane sulfonic acid for example of the SEPIGEL or SIMULGEL type sold in particular by SEPPIC,
copolymers of acrylamidomethyl/methylacrylate propane sulfonic acid of polyoxyethylene alkyl (cross-linked or not) among others of the ARISTOFLEX HMS, ARISTOFLEX TAC type, sold by CLARIANT,
copolymers of acrylamidomethyl propane sulfonic acid and of hydroxyethyl acrylate, such as for example the acrylamidomethyl propane sulfonic acid/hydroxyethyl acrylate copolymer such as in particular the one used in the commercial product sold under the name SIMULGEL NS by SEPPIC, or the acrylamidomethyl propane sulfonic acid/hydroxyethyl acrylate copolymer such as in particular the one used in the commercial product sold under the name SEPINOV EMT 10 sold by SEPPIC (INCI name: HYDROXYETHYL ACRYLATE/SODIUM ACRYLOYLDIMETHYL TAURATE COPOLYMER);
and mixtures thereof.

By way of other examples of hydrophilic polymer thickeners, mention may be made of:
anionic, cationic, amphoteric or non-ionic chitin or chitosan polymers;
cellulose polymers, in particular separate from alkylcellulose, chosen from hydroxyethylcellulose, hydroxypropylcellulose, hydroxymethylcellu lose, ethylhydroxyethylcellulose, carboxymethylcellulose, and quaternized cellulose derivatives;
vinyl polymers, such as polyvinylpyrrolidones, methylvinyl ether and malic anhydride, vinyl acetate and crotonic acid copolymer, vinylpyrrolidone and vinyl acetate copolymers; vinylpyrrolidone and caprolactam copolymers; polyvinyl alcohol;

polymers of natural origin, possibly modified, such as: galactomannans and derivatives thereof, such as Konjac gum, Gellan gum, Carob gum, Fenugrec gum, Karaya gum, Tragacanthe gum, gum arabic, gum *acacia*, guar gum, hydroxypropylguar, hydroxypropylguar modified by sodium methylcarboxylate groups (Jaguar XC97-1, Rhodia), ammonia trimethyl hydroxypropyl guar chloride, xanthan gum and the derivatives of xanthan;

alginates and carrageenans;

mucopolysaccharides such as hyaluronic acid, chondroitin sulfates;

and mixtures thereof.

According to a preferred embodiment of the invention, the thickening polymer is a acrylamidomethyl propane sulfonic acid copolymer, and in particular an acrylamidomethyl propane sulfonic acid and hydroxyethyl acrylate copolymer.

Dyes

According to one embodiment, the composition according to the invention can furthermore contain at least one coloring agent that can be chosen from water-soluble or liposoluble colorants, pigments, nacres and mixtures thereof.

The composition according to the invention can further comprise one or a plurality of dyes chosen from water-soluble or liposoluble colorants, and powder dyes such as pigments, nacres and glitter well known to those skilled in the art. The dyes may be present, in the composition, at a content ranging from 0.01% to 25% by weight, with respect to the weight of the composition, preferably from 0.01% to 20% by weight.

The term "colorants" refers to generally organic compounds soluble in fats such as oils or in an aqueous or hydroalcoholic phase.

The water-soluble dyes implemented according to the invention are more particularly water-soluble colorants.

The term "water-soluble colorant" refers to in terms of the invention, any generally organic, natural or synthetic compound, soluble in an aqueous phase or water-miscible solvents and able to dye. In particular, the term water-soluble is intended to characterize the aptitude of a compound to be solubilized in water, measured at 25° C., at a concentration at least equal to 0.1 g/l (obtaining of a macroscopically isotropic and transparent solution, colored or not). This solubility is in particular greater than or equal to 1 g/l.

In terms of hydrosoluble colorants that are suitable for the invention mention can in particular be made of synthetic or natural water-soluble colorants such as for example DC Red 6 (Lithol Rubine Na; Cl: 15850), DC Red 22 (Cl: 45380), DC Red 28 (Cl: 45410, Na salt), DC Red 30 (Cl: 73360), DC Red 33 (Cl: 17200), DC Red 40 (Cl: 16035), FDC Yellow 5 (Cl: 19140), FDC Yellow 6 (Cl: 15985), DC Yellow 8 (Cl: 45350 Na salt), FDC Green 3 (Cl: 42053), DC Green 5 (Cl: 61570), FDC Blue 1 (Cl: 42090).

Given by way of illustration and not limiting of sources of water-soluble dye(s) that can be implemented in the framework of this invention, mention can in particular be made of those of natural origin, such as extracts of carmine, cochineal, beet, grape, carrot, tomato, rocou, paprika, henna, caramel and curcumine.

As such, the water-soluble dyes that are suitable for the invention are in particular carminic acid, betanin, anthocyanins, enocyanins, lycopene, bixin, norbixin, capsanthyn, capsorubin, flovoxanthin, lutein, cryptoxanthin, rubixanthin, violaxanthin, riboflavin, roudoxanthin, cantaxanthin, chlorophyll, and mixtures thereof.

It can also be copper sulfate, iron, water-soluble sulfopolyesters, rhodamine, betaine, methylene blue, disodium tartrazine salt and disodium fuchsin salt.

Some of these water-soluble dyes are in particular approved from a food standpoint. By way of example of these colorants, more particular mention can be made of the colorants in the carotenoid family, referenced under food codes E120, E162, E163, E160a-g, E150a, E101, E100, E140 and E141.

According to a particularly preferred embodiment, the water-soluble dye(s) are chosen from the sodium salts of Yellow 6, Yellow 5, Red 6, Red 33, Red 40.

Among the liposoluble colorants, particular mention can be made of Sudan Red, DC Red 17, DC Green 6, β-carotene, Sudan Brown, DC Yellow 11, DC Violet 2, DC orange 4 (Cl: 15510, Na salt), DC Orange 5, Quinoline Yellow, Red 21, Red 27 and beta-carotene.

The term "pigments" should be understood to mean white or colored, mineral or organic particles, which are insoluble in an aqueous solution and are intended for coloring and/or opacifying the resulting film.

The pigments may be present in a proportion of 0.01% to 25% by weight, in particular from 0.01% to 20% by weight, with respect to the total weight of the cosmetic composition. The pigments can be chosen from mineral pigments, organic pigments, and composite pigments (i.e. pigments with a mineral and/or organic material base).

The pigments can be chosen from monochrome pigments, lacquers, nacres, pigments with an optical effect, such as reflective pigments and goniochromatic pigments.

Mineral pigments can be chosen from metal oxide pigments, chromium oxides, iron oxides, titanium oxide, zinc oxides, cerium oxides, zirconium oxides, manganese violet, Prussian blue, ultramarine blue, ferric blue, and mixtures thereof.

It can also be a pigment having a structure that may be, for example, of sericite/brown iron oxide/titanium dioxide/silica type. Such a pigment is marketed, for example, under the reference COVERLEAF NS or JS by CHEMICALS AND CATALYSTS and has a contrast ratio of around 30.

The dye may also comprise a pigment having a structure that may, for example, be of the type of silica microbeads containing iron oxide. An example of a pigment having this structure is marketed by MIYOSHI under the name PC BALL PC-LL-100 P, and this pigment consists of silica microbeads containing yellow iron oxide.

The organic pigments can for example be:

cochineal carmine, organic pigments with azoic, anthraquinonic, indigoid, xanthenic, pyrenic, quinolinic, triphenylmethane, fluorane colorants;

organic lacquers or insoluble salts of sodium, of potassium, of calcium, of barium, of aluminum, of zirconium, of strontium, of titanium, of acid colorants such as the azoic, anthraquinonic, indigoid, xanthenic, pyrenic, quinolinic, triphenylmethane, fluorane colorants. These colorants generally contain at least one carboxylic or sulfonic acid group;

melanic pigments.

Among the organic pigments, mention can be made of D&C Blue no. 4, D&C Brown no. 1, D&C Green no. 5, D&C Green no. 6, D&C Orange no. 4, D&C Orange no. 5, D&C Orange no. 10, D&C Orange no. 11, D&C Red no. 7 (Calcium salt of Lithol Rubine), D&C Red no. 17, D&C Red no. 21, D&C Red no. 22, D&C Red no. 27, D&C Red no.

28, D&C Red no. 30, D&C Red no. 31, D&C Red no. 33, D&C Red no. 34, D&C Red no. 36, D&C Violet no. 2, D&C Yellow no. 7, D&C Yellow no. 8, D&C Yellow no. 10, D&C Yellow no. 11, FD&C Blue no. 1, FD&C Green no. 3, FD&C Red no. 40, FD&C Yellow no. 5, FD&C Yellow no. 6.

Along the organic lacquers, mention can be made of organic lacquers supported by an organic support such as colophony or aluminum benzoate, for example. Preferably, among the organic lacquers, mention can in particular be made of those known under the following names: D&C Red no. 2 Aluminum lake, D&C Red no. 3 Aluminum lake, D&C Red no. 4 Aluminum lake, D&C Red no. 6 Aluminum lake, D&C Red no. 6 Barium lake, D&C Red no. 6 Barium/Strontium lake, D&C Red no. 6 Strontium lake, D&C Red no. 6 Potassium lake, D&C Red no. 7 Aluminum lake, D&C Red no. 7 Barium lake, D&C Red no. 7 Calcium lake, D&C Red no. 7 Calcium/Strontium lake, D&C Red no. 7 Zirconium lake, D&C Red no. 8 Sodium lake, D&C Red no. 9 Aluminum lake, D&C Red no. 9 Barium lake, D&C Red no. 9 Barium/Strontium lake, D&C Red no. 9 Zirconium lake, D&C Red no. 10 Sodium lake, D&C Red no. 19 Aluminum lake, D&C Red no. 19 Barium lake, D&C Red no. 19 Zirconium lake, D&C Red no. 21 Aluminum lake, D&C Red no. 21 Zirconium lake, D&C Red no. 22 Aluminum lake, D&C Red no. 27 Aluminum lake, D&C Red no. 27 Aluminum/Titanium/Zirconium lake, D&C Red no. 27 Barium lake, D&C Red no. 27 Calcium lake, D&C Red no. 27 Zirconium lake, D&C Red no. 28 Aluminum lake, D&C Red no. 30 lake, D&C Red no. 31 Calcium lake, D&C Red no. 33 Aluminum lake, D&C Red no. 34 Calcium lake, D&C Red no. 36 lake, D&C Red no. 40 Aluminum lake, D&C Blue no. 1 Aluminum lake, D&C Green no. 3 Aluminum lake, D&C Orange no. 4 Aluminum lake, D&C Orange no. 5 Aluminum lake, D&C Orange no. 5 Zirconium lake, D&C Orange no. 10 Aluminum lake, D&C Orange no. 17 Barium lake, D&C Yellow no. 5 Aluminum lake, D&C Yellow no. 5 Zirconium lake, D&C Yellow no. 6 Aluminum lake, D&C Yellow no. 7 Zirconium lake, D&C Yellow no. 10 Aluminum lake, FD&C Blue no. 1 Aluminum lake, FD&C Red no. 4 Aluminum lake, FD&C Red no. 40 Aluminum lake, FD&C Yellow no. 5 Aluminum lake and FD&C Yellow no. 6 Aluminum lake.

The pigments can be treated by a hydrophobic agent.

The hydrophobic treatment agent can be chosen from silicones such as methicones, dimethicones, perfluoroalkylsilanes; fatty acids such as stearic acid; metallic soaps such as aluminum dimyristate, the aluminum salt of hydrogenated tallow glutamate, perfluoroalkyl phosphates, perfluoroalkyl silanes, perfluoroalkyl silazanes, hexafluoropropylene polyoxides, polyorganosiloxanes comprising perfluoroalkyl perfluoropolyethers groups, amino acids; N-acylated amino acids or salts thereof; lecithin, isopropyl triisostearyl titanate and mixtures thereof.

The N-acylated amino acids may comprise an acyl group having 8 to 22 carbon atoms, such as for example a 2-ethyl hexanoyl, caproyl, lauroyl, myristoyl, palmitoyl, stearoyl, cocoyl group. The salts of these compounds may be aluminum, magnesium, calcium, zirconium, zinc, sodium, potassium salts. The amino acid may be for example lysine, glutamic acid, alanine.

The term alkyl mentioned in the above-mentioned compounds particularly denotes an alkyl group having 1 to 30 carbon atoms, preferably having 5 to 16 carbon atoms.

Hydrophobic treated pigments are in particular described in application EP-A-1086683.

The term "nacres" should be understood to mean iridescent or non-iridescent colored particles of any shape which are in particular produced by certain mollusks in their shell or else are synthesized and which exhibit a color effect by optical interference.

The nacres may be selected from pearlescent pigments such as titanium mica coated with iron oxide, titanium mica coated with bismuth oxychloride, titanium mica coated with chromium oxide, titanium mica coated with an organic dye, and pearlescent pigments based on bismuth oxychloride. This may also involve mica particles at the surface whereof are superposed at least two successive layers of metal oxides and/or of organic dyes.

By way of example of nacres, mention may also be made of natural mica coated with titanium oxide, with iron oxide, with natural pigment or with bismuth oxychloride.

Among the nacres available on the market, mention may be made of the TIMICA, FLAMENCO and DUOCHROME nacres (based on mica) marketed by ENGELHARD, the TIMIRON nacres marketed by MERCK, the nacres based on mica, PRESTIGE, marketed by ECKART and the nacres based on synthetic mica, SUNSHINE, marketed by SUN CHEMICAL.

The nacres may more particularly possess a yellow, pink, red, bronze, orange, brown, gold and/or copper color or glint.

By way of illustration of nacres which can be used in the context of the invention, mention may, in particular, be made of the gold nacres marketed, in particular, by ENGELHARD, under the name Brilliant gold 212G (Timica), Gold 222C (Cloisonne), Sparkle gold (Timica), Gold 4504 (Chromalite) and Monarch gold 233X (Cloisonne); the bronze nacres, marketed, in particular, by MERCK under the name Bronze fine (17384) (Colorona) and Bronze (17353) (Colorona) and by ENGELHARD under the name Super bronze (Cloisonne); the orange nacres, in particular, marketed by ENGELHARD under the name Orange 363C (Cloisonne) and Orange MCR 101 (Cosmica) and by MERCK under the name Passion orange (Colorona) and Matte orange (17449) (Microna); the brown-hued nacres marketed in particular by ENGELHARD under the name Nu-antique copper 340XB (Cloisonne) and Brown CL4509 (Chromalite); the copper-glint nacres marketed in particular by ENGELHARD under the name Copper 340A (Timica); the red-glint nacres marketed in particular by MERCK under the name Sienna fine (17386) (Colorona); the yellow-glint nacres marketed in particular by ENGELHARD under the name Yellow (4502) (Chromalite); the gold-glint red-hued nacres marketed in particular by ENGELHARD under the name Sunstone G012 (Gemtone); the pink nacres marketed in particular by ENGELHARD under the name Tan opal G005 (Gemtone); the gold-glint black nacres marketed in particular by ENGELHARD under the name Nu-antique bronze 240 AB (Timica), the blue nacres marketed in particular by MERCK under the name Matte blue (17433) (Microna), the silver-glint white nacres marketed in particular by MERCK under the name Xirona Silver and the green-gold and pinkish orangish nacres marketed in particular by MERCK under the name Indian summer (Xirona) and mixtures thereof.

The cosmetic composition according to the invention may also contain at least one material with a specific optical effect.

This effect is different from a simple conventional hue effect, i.e. a unified and stabilized effect of the kind produced by conventional dyes, such as, for example, monochromatic pigments. For the purpose of the invention, the term "stabilized" signifies absence of an effect of variability of color with the angle of observation or in response to a temperature change.

For example, this material may be selected from particles having a metallic glint, goniochromatic coloring agents, diffracting pigments, thermochromatic agents, optical brighteners, and also fibers, in particular of the interference type. Of course, these various materials may be combined so as to provide the simultaneous manifestation of two effects, or even a new effect in accordance with the invention.

The metallic-glint particles that can be used in the invention are in particular chosen from:
  particles of at least one metal and/or of at least one metal derivative,
  particles comprising a single-substance or multi-substance, organic or mineral substrate, at least partially coated with at least one metallic-glint layer comprising at least one metal and/or at least one metal derivative, and
  mixtures of said particles.

Among the metals that may be present in said particles, mention may, for example, be made of Ag, Au, Cu, Al, Ni, Sn, Mg, Cr, Mo, Ti, Zr, Pt, Va, Rb, W, Zn, Ge, Te, Se and mixtures or alloys thereof. Ag, Au, Cu, Al, Zn, Ni, Mo, Cr and mixtures or alloys thereof (for example, bronzes and brasses) are preferred metals.

The term "metal derivatives" denotes compounds derived from metals, in particular oxides, fluorides, chlorides and sulfides By way of illustration of these particles, mention may be made of aluminum particles, such as those marketed under the trade names STARBRITE 1200 EAC® by SIBERLINE and METALURE® by ECKART.

Mention may also be made of metal powders of copper or of alloy mixtures, such as the references 2844 marketed by RADIUM BRONZE, metal pigments, such as aluminum or bronze, for instance those marketed under the trade name ROTOSAFE 700 by ECKART, silica-coated aluminum particles marketed under the trade name VISIONAIRE BRIGHT SILVER bye ECKART and metal alloy particles, such as silica-coated bronze (copper and zinc alloy) marketed under the trade name Visionaire Bright Natural Gold by Eckart.

The particles in question may also be particles comprising a glass substrate, such as those marketed by NIPPON SHEET GLASS under the trade name MICROGLASS METASHINE.

The goniochromatic coloring agent may be selected, for example, from multilayer interference structures and liquid-crystal coloring agents.

Examples of symmetrical multilayer interference structures that may be used in compositions prepared according to the invention are, for example, the following structures: $Al/SiO_2/Al/SiO_2/Al$, pigments having this structure being marketed by DUPONT DE NEMOURS; $Cr/MgF_2/Al/MgF_2/Cr$, pigments having this structure being marketed under the trade name CHROMAFLAIR by FLEX; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being marketed under the trade name SICOPEARL by BASF; $MoS_2/SiO_2/mica$-oxide$/SiO_2/MoS_2$; $Fe_2O_3/SiO_2/mica$-oxide$/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being marketed under the trade name XIRONA by MERCK (Darmstadt). By way of example, these pigments may be the pigments with a silica/titanium oxide/tin oxide structure marketed under the name XIRONA MAGIC by MERCK, pigments with a silica/brown iron oxide structure marketed under the name XIRONA INDIAN SUMMER by MERCK and pigments with a silica/titanium oxide/mica/tin oxide structure marketed under the name XIRONA CARRIBEAN BLUE by MERCK. Mention may also be made of the INFINITE COLORS pigments from SHISEIDO. Depending on the thickness and the nature of the various layers, various effects are obtained. Thus, with the structure $Fe_2O_3/SiO_2/Al/SiO_2/Fe_2O_3$, the color changes from green-golden to red-gray for $SiO_2$ layers from 320 to 350 nm; from red to golden for $SiO_2$ layers from 380 to 400 nm; from violet to green for $SiO_2$ layers from 410 to 420 nm; from copper to red for $SiO_2$ layers from 430 to 440 nm.

By way of example of pigments with a polymeric multilayer structure, mention may be made of those marketed by 3M under the trade name COLOR GLITTER.

Examples of liquid-crystal goniochromatic particles that may be used include those sold by CHENIX, and also that marketed under the trade name HELICONE® HC by WACKER.

Polyols

The composition according to the invention may also comprise at least one polyol, more particularly a liquid polyol at ambient temperature, $C_2$-$C_8$, preferably $C_3$-$C_6$, saturated or not, linear or branched, comprising from 2 to 6 hydroxyl groups.

Preferably, the polyol is chosen from glycerin, diglycerin, pentanediol, $C_3$-$C_{08}$ glycols, linear or branched, saturated, in particular propylene glycol, butylene glycol, pentylene glycol, caprylyl glycol, dipropylene glycol, as well as mixtures thereof, and preferably glycerin, propyleneglycol, butyleneglycol, and mixtures thereof.

The composition according to the invention if it contains any, has a content in polyol(s) particularly comprised between 2 and 10% by weight, preferably from 4 to 8% by weight, with respect to the weight of the composition Usual Additional Cosmetic Ingredients The composition according to the invention can further comprise any usual cosmetic ingredient that can be chosen in particular from the hydrophobic thickeners, fillers of an organic or mineral nature, antioxidants, perfumes, preservatives, neutralizers, sequestering agents, surfactants in particular non-ionic, having an HLB greater than 8, film-forming agents, active ingredients, and mixtures thereof.

Obviously, those skilled in the art will take care to choose these optional additional ingredients, and/or the quantity thereof, such that the advantageous properties of the active constituents of the composition according to the invention are not, or are substantially not, altered by the envisaged addition.

The hydrophobic thickener can be chosen from alkylated guar gums (with a C1-C6 alkyl group), such as those described in EP-A-708114; oil gelling agent polymers such as triblock polymers or as a star resulting from the polymerization or copolymerization of at least one monomer with an ethylene group, such as the polymers sold under the name Kraton; resins of polyamides comprising alkyl groups having from 12 to 22 carbon atoms, such as those described in U.S. Pat. No. 5,783,657; polysaccharide alkylethers, in particular of which the alkyl group comprises from 1 to 24 carbon atoms, preferably from 1 to 10, better from 1 to 6, and more specifically from 1 to 3, such as those described in document EP-A-898958; organophilic clays; hydrophobic pyrogenic silicas; hydrophobic silica aerogels; elastomeric organopolysiloxanes and mixtures thereof.

The clays are silicates that contain a cation that can be chosen from the cations of calcium, magnesium, aluminum, sodium, potassium, lithium and mixtures thereof. As examples of such products, mention can be made of clays of the family of smectites such as montmorillonites, hectorites, bentonites, beidellites, saponites, as well as of the family of vermiculites, stevensite, chlorites. These clays may be of natural or synthetic origin. Organophilic clays are clays modified with a chemical compound chosen from the quaternary amines, tertiary amines, acetate amines, imidazolines, amine soaps, fatty sulfates, alkyl aryl sulfonates, amide oxides, and mixtures thereof.

Mention can as such be made of hectorites modified by a quaternary amine, more precisely by a halide, such as a $C_{10}$ to $C_{22}$ fatty acid ammonium chloride, such as hectorite modified by di-stearyl di-methyl ammonium chloride (CTFA name: Disteardimonium hectorite), such as, for example, the one sold under the name Bentone 38V®, Bentone 38V CG, Bentone EW CE, by ELEMENTIS; the stearalkonium Hectorites such as Bentone 27 V, Mention can also be made of quaternium-18 bentonites such as those sold under the names Bentone 34 sold by Elementis, Claytone 40, Tixogel VP by United catalyst by Southern Clay; stearalkonium bentonites such as those sold under the names Tixogel LG by United Catalyst, Claytone AF, Claytone APA by Southern Clay; quaternium-18/benzalkonium bentonite such as those sold under the name Claytone HT by Southern Clay According to a preferred embodiment, the thickening agent is chosen from modified organophilic clays, in particular modified organophilic hectorites, in particular by halides, preferably ammonium benzyldimethyl stearate chlorides, or by distearyl dimethyl ammonium chloride.

The hydrophobic pyrogenic silicas can be obtained by modifying the surface of the silica by a chemical reaction that generates a decrease in the number of silanol groups, with these groups in particular able to be substituted with hydrophobic groups.

The hydrophobic groups may be:
trimethylsiloxyl groups, particularly obtained by treating pyrogenic silica in the presence of hexamethyldisilazane. Silicas treated in this way are referred to as "Silica silylate" as per the CTFA (6th edition, 1995). They are for example sold under the references "AEROSIL R812®" by Degussa, "CAB-O-SIL TS-530®" by Cabot,
dimethylsilyloxyl or polydimethylsiloxane groups, particularly obtained by treating pyrogenic silica in the presence of polydimethylsiloxane or dimethyldichlorosilane. Silicas treated in this way are referred to as "Silica dimethyl silylate" as per the CTFA (6th edition, 1995). They are for example sold under the references "AEROSIL R972®", "AEROSIL R974®" by Degussa, "CAB-O-SIL TS-610®", "CAB-O-SIL TS-720®" by Cabot.
The silica aerogels are porous materials obtained by replacing (via drying) the liquid component of a silica gel with air. They are generally synthesized by the sol-gel method in a liquid medium then dried usually via the extraction of a supercritical fluid, with the most commonly used being supercritical $CO_2$. This type of drying makes it possible to prevent the contraction of the pores and of the material. The sol-gel method and the various dryings are described in detail in Brinker C J., and Scherer G. W., Sol-Gel Science: New York: Academic Press, 1990.
Particles of hydrophobic silica aerogels modified on the surface by trimethylsilyl groups will preferably be used.
As hydrophobic silica aerogels, mention can be made for example of the aerogel sold under the name VM-2260 (INCI name Silica silylate), by Dow Corning, of which the particles have an average size of about 1000 microns and a specific area per unit mass ranging from 600 to 800 $m^2/g$. Mention can also be made of the aerogels sold by Cabot under the references AEROGEL TLD 201, AEROGEL OGD 201, AEROGEL TLD 203, ENOVA® AEROGEL MT 1100, ENOVA AEROGEL MT 1200.

The elastomeric organopolysiloxanes are in general partially or totally cross-linked and possibly of a three-dimensional structure. The elastomeric organopolysiloxanes associated with a fatty phase generally have the form of a gel comprised of an elastomeric organopolysiloxane associated with a fatty phase, included in at least one hydrocarbon oil and/or a silicone oil. They can be chosen in particular from the cross-linked polymers described in application EP-A-0295886. According to this application, the elastomeric organopolysiloxanes are obtained par by addition reaction and cross-linking of at least:
(a) an organopolysiloxane having at least two lower alkenyl groups per molecule;
(b) an organopolysiloxane having at least two hydrogen atoms bound to a silicon atom per molecule; and
(c) and a catalyst of the platinum type.

The additional thickening agent may be present at a content ranging from 0.1% to 20% by weight, in relation to the total weight of the preferably ranging from 0.1% to 10% by weight.

The term "filler" should be understood to mean colorless or white solid particles of any shape, which are in a form that is insoluble or dispersed in the medium of the composition. They are separate from the dyes.

Among the fillers that can be used in the compositions according to the invention, mention can be made of silica, kaolin, starch, lauroyl-lysine, particles of pyrogenic silica, possibly with hydrophilic treatment, mica, talc, sericite, polyamide powders (Nylon®), poly-p-alanine and polyethylene, powders of tetrafluoroethylene polymers (Teflon®), the polymeric hollow microbeads such as those of polyvinylidene/acrylonitrile chloride such as Expancel® (Nobel Industrie), of copolymers of acrylic acid, silicone resin microbeads (Tospearls® from Toshiba, for example), elastomer polyorganosiloxane particles, precipitated calcium carbonate, magnesium carbonate and hydro-carbonate, hydroxyapatite, barium sulfate, aluminum oxides, polyurethane powders, composite fillers, hollow silica microbeads, glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate and mixtures thereof.

A composition implemented according to the invention may comprise one or more fillers at a content ranging from 0.1% to 15% by weight, particularly from 1 to 10% by weight with respect to the weight of the composition.

The composition according to the invention can further comprise at least one active ingredient.

The term "active ingredient" refers to a compound that has a cosmetic and/or dermatological effect, in particular on the lips. This active ingredient can be hydrophilic or hydrophobic. The active ingredient can be water-soluble.

As such, the active ingredient present in the composition according to the invention can be independently chosen from among the agents that stimulate the synthesis of dermal or epidermal macromolecules and/or prevent their degradation, anti-irritant agents, anti-pollution or anti-radical agents, UV filters, vitamins A, E, C, B3, provitamins such as D-panthenol, thickening agents, such as α-bisabolol, aloe vera, allantoin, plant extracts or essential oils, agents acting on microcirculation, agents acting on the energy metabolism of cells, healing agents, freshening agents such as menthol and the derivatives thereof, and mixtures thereof.

Mention can also be made of moisturizing agents, different from the aforementioned polyols, such as for example hyaluronic acid and the salts thereof, beads of hyaluronic acid such as those sold by Engelhard Lyon, sorbitol, xylitol, glycerol polyacrylate, ectoin and the derivatives thereof, collagen and chondroitin sulfate beads and of marine origin (Ateocollagen) sold by Engelhard Lyon under the name marine filling beads, a C-glycoside derivative such as those described in application WO 02/051828 and in particular CGβDxylopyranoside2hydroxypropane in the form of a 30% solution by weight in active material in a water/propylene glycol mixture (60/40% by weight) such as the product manufactured by CHIMEX under the trade name "MEXORYL SBB®"; plant extracts in an aqueous or oily medium such as in particular pomegranate extract, the aqueous solutions obtained using *Cocos nucifera*; sphingolipids, such as ceramide 5; and mixtures thereof.

The quantity of active ingredient(s) ranges for example from 0.0001 to 8% by weight and preferably from 0.01 to 5% by weight of active material with respect to the total weight of the composition.

The product according to the invention can be advantageously used as a makeup product for the skin and/or of the lips according to the nature of the ingredients used. In particular, the product of the invention can have the form of a solid foundation, a stick of lipstick, of an anti-wrinkle product or eye contour, eye liner, eye shadows, makeup product for the body.

Preferably, the composition of the invention can have the form of a colored makeup product for the lips such as a stick of lipstick or a lip gloss, optionally having care or treatment properties.

The compositions of the invention can be obtained by heating various constituents to a temperature that corresponds to the highest melting temperature of the ingredient or ingredients, then casting of the melted mixture in a mold.

The composition according to the invention can be manufactured by known methods, generally used in the cosmetics or dermatological field. For example, it can be manufactured via the following method:

The dyes can be ground in a portion of the oily phase.

Independently, the oils, waxes and surfactants, in particular with an HLB less than or equal to 8, if they are present, are mixed, in particular under stirring, at a temperature such that the ingredients are in liquid form, for example at a temperature greater than 70° C. Then, the silicon resin is introduced into the mixture. Then the silicone polyamide is introduced. Finally, the ground product of dyes can then be added into the mixture constituting the oily phase.

The aqueous phase is also prepared by mixing water-soluble ingredients, then it can be heated, for example to a temperature greater than 70° C.

The, in particular under stirring and heating, the aqueous phase is introduced into the oily phase.

Finally, the composition can be cast, for example in a mold able to give it the shape of a stick and the whole can be left to cool.

According to another aspect, the invention also relates to a cosmetic assembly comprising:
i) a receptacle that delimits a compartment, said receptacle being closed by a closing element; and
ii) a composition in accordance with the invention arranged inside said compartment.

The receptacle can be of any suitable shape. It is in particular in the form of a pot, a case or a box. Preferably, the receptacle is sealed.

The closing element can be in the form of a removable cap, of a lid, of a seal, of a strip that can be torn, or of a capsule, in particular of the type comprising a body fixed to the receptacle and a hinged cap on the body. It can also have the form of an element providing the selective closing of the receptacle, in particular a pump, a valve, such as a non-return valve for example.

The examples hereinafter are given by way of illustration and are not intended to restrict this invention. The percentages are percentages by weight.

EXAMPLES 1 AND 2 OF LIPSTICKS ACCORDING TO THE INVENTION

The solid inverted emulsion compositions of the examples 1 and 2 are obtained according to the following protocol:

In a first step, the fillers and the pigments are ground in a portion of the oily phase.

The remainder of the liposoluble ingredients and possibly the surfactants (cetyl PEG/PGG-10/1 dimethicone, PEG/PPG-18/18 dimethicone and polyglycerol-4 isostearate) are then mixed at a temperature of about 95-100° C. The ground product or the pre-dispersed active ingredients are then added into the oily phase.

The aqueous phase is prepared at 85° C. and dispersed using a Rayneri deflocculator.

Finally, the composition is cast into a mold in order to give it the shape of a stick and the whole is cooled at 0° C. The sticks are unmolded at 0° C. and left at ambient temperature.

| Compound (INCI name) | Example 1 | Example 2 |
|---|---|---|
| Dyes (pigments, lacquers and or titanium oxide) | 8 | 8 |
| Phenyltrimethicone (KF 56 A, from Shin Etsu) | 13.5 | 10.3 |
| Isononyl isononanoate | 10.9 | 8.4 |
| Candelilla wax (7820 Light Special Candelilla REAL ® from Multiceras) | 2.5 | 2.6 |
| C20-40 alkyl stearate (Kester Wax K 82 H from Koster Keunen) | 7.5 | 7.9 |
| Trimethylsiloxysilicate (SR1000 from Momentive Performance Materials) | 8.5 | 8.5 |
| Octyldodecanol | 13.4 | — |
| CETYL PEG/PPG-10/1 DIMETHICONE (Abil EM-90 from Evonik Goldschmidt) | — | 3 |
| PEG/PPG-18/18 dimethicone in dimethicone (X-22-6711D, from Shin Etsu; in dimethicone; 25% active material) | — | 1 |
| Polyglycerol-4 isostearate (Isolan GI 34 from Goldschmidt) | — | 1 |
| NYLON-611/DIMETHICONE COPOLYMER (DC 2-8179 from Dow Corning) | 5.7 | 5.7 |
| Glycerin | 5 | 5 |
| HYDROXYETHYL ACRYLATE/SODIUM ACRYLOYLDIMETHYL TAURATE COPOLYMER (SEPINOV EMT 10 from SEPPIC) | 0.2 | 0.2 |
| EDTA | 0.2 | 0.2 |
| Octane-1,2-diol | — | 0.5 |
| Sodium hyaluronate | 0.1 | 0.1 |
| Water | Qs 100 | Qs 100 |

For example 1 a stick of a hardness of 37 $Nm^{-1}$ is obtained.

For example 2 a stick of a hardness of 42 Nm$^{-1}$ is obtained.

The two compositions are applied easily, with a good slip and make it possible to obtain a covering deposit, intense, fine and homogeneous on the first pass, fresh, not tacky, not migrant (especially after 1 h30), of good stability, in particular for the color, and comfortable. The color of the deposit is uniform with good covering power.

Example 3 of a Lipstick According to the Invention

The solid inverted emulsion composition of example 3 (according to the invention) is obtained according to the following protocol:

In a first step, the dyes are ground in a part of the hydrocarbon-based oils.

The remainder of the oils is heated at 95° C. and the wax, the silicon resin and the nylon-611/dimethicone are then successively added under mixing (Rayneri) until the resulting mixture is homogeneous.

The mixture of dyes and part of the hydrocarbon-based oils is then added into the oily phase.

The aqueous phase is separately prepared at 85° C. then dispersed in the oily phase (Rayneri).

Finally, the composition is cast into a mold in order to give it the shape of a stick and the whole is cooled at 0° C. The sticks are unmolded at 0° C. left at ambient temperature.

| Compound (INCI name) | Example 3 |
|---|---|
| Yellow 6 Lake/Alumina | 3.9 |
| Red 7 | 0.3 |
| Titanium dioxide | 0.5 |
| Red 28 Lake | 3.3 |
| Phenyltrimethicone (KF 56 A, from Shin Etsu) | 13.5 |
| Isononyl isononanoate | 10.9 |
| C20-40 alkyl stearate (Kester Wax K 82 H from Koster Keunen) | 8 |
| Trimethylsiloxysilicate (SR1000 from Momentive Performance Materials) | 8.5 |
| Octyldodecanol | 13.4 |
| NYLON-611/DIMETHICONE COPOLYMER (DC 2-8179 from Dow Corning) | 5.7 |
| Glycerin | 5 |
| HYDROXYETHYL ACRYLATE/SODIUM ACRYLOYLDIMETHYL TAURATE COPOLYMER (SEPINOV EMT 10 from SEPPIC) | 0.2 |
| EDTA | 0.2 |
| Sodium hyaluronate | 0.1 |
| Water | Qs 100 |

For example 3 a stick of a hardness of around 26 Nm$^{-1}$ is obtained.

The stick is homogenous and smooth.

Comparative Lipstick Examples A and B

The comparative compositions (i.e. comparative lipsticks) A and B are obtained according to the protocol described in example 3.

Comparative composition A corresponds to the composition of example 3 except that the wax is substituted by an alcohol wax, i.e. C30-50 alcohols (Performacol 550 Alcohol) which have a melting point of around 95° C. The melting point is greater than 90° C.

Comparative composition B corresponds to the composition of example 3 except that the wax is substituted by an apolar wax, i.e. polyethylene wax (PERFORMALENE 500-L POLYETHYLENE of New Phase Technologies) which has a melting point of around 77° C. The wax is thus not polar.

| Compound (INCI name) | Comparative lipstick A | Comparative lipstick B |
|---|---|---|
| Yellow 6 Lake/Alumina | 3.9 | 3.9 |
| Red 7 | 0.3 | 0.3 |
| Titanium dioxide | 0.5 | 0.5 |
| Red 28 Lake | 3.3 | 3.3 |
| Phenyltrimethicone (KF 56 A, from Shin Etsu) | 13.5 | 13.5 |
| Isononyl isononanoate | 10.9 | 10.9 |
| C30-50 Alcohols (Performacol 550 Alcohol of Baker Hughes) | 8 | — |
| Polyethylene wax (PERFORMALENE 500-L POLYETHYLENE of New Phase Technologies) | — | 8 |
| Trimethylsiloxysilicate (SR1000 from Momentive Performance Materials) | 8.5 | 8.5 |
| Octyldodecanol | 13.4 | 13.4 |
| NYLON-611/DIMETHICONE COPOLYMER (DC 2-8179 from Dow Corning) | 5.7 | 5.7 |
| Glycerin | 5 | 5 |
| HYDROXYETHYL ACRYLATE/SODIUM ACRYLOYLDIMETHYL TAURATE COPOLYMER (SEPINOV EMT 10 from SEPPIC) | 0.2 | 0.2 |
| EDTA | 0.2 | 0.2 |
| Sodium hyaluronate | 0.1 | 0.1 |
| Water | Qs 100 | Qs 100 |

Comparative lipstick A with a hardness of 48+/−2.7 Nm$^{-1}$ is obtained. However the stick is not smooth, and comprises deep stretches and irregularities. Indeed the emulsion is very thick, and is not homogenously put in molds.

Comparative lipstick B with a hardness of 69+/−1.2 Nm$^{-1}$ is obtained. However, the stick comprises irregularities, cavities and air bubbles at the surface of the stick. Again, the emulsion is thick, and is not homogenously put in molds.

The invention claimed is:

1. A solid cosmetic composition for makeup or treatment comprising:
 a continuous fatty phase comprising at least one nylon-611/dimethicone copolymer in an amount of 2% to 9% by weight in relation to the total weight of the composition, at least one silicone resin in an amount 5% to 15% by weight in relation to the total weight of the composition, at least one non-volatile polar hydrocarbon-based oil present in a quantity between 5 and 30% by weight in relation to the total weight of the composition and at least one polar wax with a melting point less than or equal to 90° C.; and
 an aqueous phase dispersed in the continuous fatty phase, the at least one silicon resin being a trimethylsiloxysilicate resin,
 the at least one non-volatile polar hydrocarbon-based oil is chosen from:
 $C_{10}$-$C_{26}$ alcohols;
 monoesters comprising between 17 and 40 carbon atoms in total, having formula $R_1COOR_2$ wherein $R_1$ is the remainder of a linear or branched or aromatic fatty acid comprising from 4 to 40 carbon atoms, saturated or not, and $R_2$ is a hydrocarbon chain containing from 3 to 40 carbon atoms with the condition that the ester comprises between 17 and 40 carbon atoms in total;

di-alkyl carbonates, with the 2 alkyl chains able to be identical or different, and
mixtures thereof,
the at least one polar wax is chosen from waxes having formula $R_1COOR_2$ wherein $R_1$ and $R_2$ are aliphatic linear, branched chains of which the number of atoms varies from 10 to 40 that can contain an oxygen atom, and of which the melting point temperature varies from 30 to 90° C., beeswax, synthetic beeswax, carnauba wax, candellila wax, lanolin wax, rice bran wax, Ouricury wax, Alfa wax, berry wax, shellac wax, cork fiber wax, sugarcane wax, Japan wax, sumac wax, montan wax, Orange wax, Lemon wax, Bay leaf wax, sunflower wax, hydrogenated Jojoba oil, hydrogenated sunflower oil, hydrogenated castor oil, hydrogenated coconut oil, waxes obtained by hydrogenating castor oil with cetyl alcohol and waxes obtained by hydrogenating olive oil with stearyl alcohol, and said wax representing 7% to 13% by weight with respect to the total weight of said composition, and
the aqueous phase comprises at least 7% by weight water with respect to the total weight of the composition.

2. The composition according to claim 1, comprising 7% to 40% by weight water with respect to the total weight of the composition.

3. The composition according to claim 1, having a hardness from 20 to 90 $Nm^{-1}$.

4. The composition according to claim 1, wherein said silicone resin is present in a ratio such that the silicon resin/nylon-611/dimethicone copolymer mass proportion is between 1 and 7/3.

5. The composition according to claim 1, wherein the at least one polar wax is chosen from waxes of which the melting point is between 30° C. and 80° C.

6. The composition according to claim 1, which comprises at least one additional oil chosen from volatile or non-volatile silicon oils, volatile or non-volatile hydrocarbon non-polar oils, and mixtures thereof.

7. The composition according to claim 6, wherein the content in additional oil(s) represents from 1 to 30% by weight, with respect to the weight of the composition.

8. The composition according to claim 6, wherein the at least one additional oil comprises a non-volatile non-polar silicon or a non-volatile non-polar hydrocarbon oil.

9. The composition according to claim 8, which comprises at least one volatile hydrocarbon or silicone oil, or mixtures thereof.

10. The composition according to claim 6, which comprises at least one additional volatile silicon or hydrocarbon oil, or mixtures thereof.

11. The composition according to claim 1, which comprises at least one aqueous phase thickening polymer.

12. The composition according to claim 1, comprising at least one hydrocarbon or silicone non-ionic surfactant, with an HLB less than or equal to 8.

13. The composition according to claim 12, wherein the content in surfactant(s) represents from 0.1 to 20% by weight in relation to the total weight of the composition.

14. A method for makeup or treatment of keratin materials which comprises applying on the keratin materials the composition according to claim 1.

15. The composition according to claim 1, which comprises 5 to 25% by weight of the at least one non-volatile polar hydrocarbon-based oil with respect to the total weight of the composition.

16. The composition according to claim 1, wherein the at least one polar wax is chosen from waxes having formula $R_1COOR_2$ wherein $R_1$ and $R_2$ are aliphatic linear, branched chains of which the number of atoms varies from 10 to 40 that can contain an oxygen atom, beeswax, synthetic beeswax, carnauba wax, candellila wax, lanolin wax, rice bran wax, Ouricury wax, Alfa wax, berry wax, shellac wax, cork fiber wax, sugarcane wax, Japan wax, sumac wax, montan wax, Orange wax, Lemon wax, Bay leaf wax, sunflower wax and hydrogenated Jojoba oil.

17. The composition according to claim 1, wherein the at least one polar wax is chosen from C20-40 alkyl stearate, beeswax, synthetic beeswax, carnauba wax, candellila wax, lanolin wax, rice bran wax, Ouricury wax, Alfa wax, berry wax, shellac wax, cork fiber wax, sugarcane wax, Japan wax, sumac wax, montan wax, Orange wax, Lemon wax, Bay leaf wax, sunflower wax and hydrogenated Jojoba oil.

18. The composition according to claim 1, which free from any volatile linear alkane.

* * * * *